US010360781B2

(12) United States Patent
Noda et al.

(10) Patent No.: US 10,360,781 B2
(45) Date of Patent: Jul. 23, 2019

(54) DISPLAY DEVICE AND DISPLAY METHOD FOR MONITORED-PERSON MONITORING SYSTEM, AND MONITORED-PERSON MONITORING SYSTEM

(71) Applicant: Konica Minolta, Inc., Tokyo (JP)

(72) Inventors: Atsuhiro Noda, Ashiya (JP); Masanori Yamashita, Toyonaka (JP); Aki Tsuji, Kyoto (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 15/561,864

(22) PCT Filed: Mar. 2, 2016

(86) PCT No.: PCT/JP2016/056475
§ 371 (c)(1),
(2) Date: Sep. 26, 2017

(87) PCT Pub. No.: WO2016/152427
PCT Pub. Date: Sep. 29, 2016

(65) Prior Publication Data
US 2018/0122207 A1    May 3, 2018

(30) Foreign Application Priority Data

Mar. 26, 2015   (JP) .................. 2015-065286

(51) Int. Cl.
G08B 21/00      (2006.01)
G08B 21/02      (2006.01)
(Continued)

(52) U.S. Cl.
CPC ........ *G08B 21/0294* (2013.01); *A61B 5/0022* (2013.01); *A61B 5/743* (2013.01);
(Continued)

(58) Field of Classification Search
CPC ................ A61G 12/00; G08B 21/0208; G08B 21/0294; A61B 5/0022; A61B 5/743; A61B 5/7465; A61B 5/748
(Continued)

(56) References Cited

U.S. PATENT DOCUMENTS 6,396,506 B1 *   5/2002   Hoshino ............. G06F 3/04855
                                                    345/650
7,237,251 B1 *   6/2007   Oz ....................... H04N 5/4401
                                                    348/E5.006
(Continued)

FOREIGN PATENT DOCUMENTS

JP    2007-074606 A    3/2007
JP    2014-090913 A    5/2014
JP    2014-158228 A    8/2014

OTHER PUBLICATIONS (translation) MAVERA 2 Instruction Manual: Detailed Edition; Kyocera Corp.; Nov. 2014; p. 136, 161, 169-170.
(Continued)

Primary Examiner — Mark S Rushing
(74) Attorney, Agent, or Firm — BakerHostetler

(57) ABSTRACT

A display device in a monitored-person monitoring system according to the present invention is a device for a monitored-person monitoring system in which each of a plurality of monitored persons is sensed and the plurality of monitored persons is monitored, the device receiving and displaying monitoring information on the monitored person. While a monitoring information display screen expressing the monitoring information on a certain monitored person among the plurality of monitored persons is displayed, even if the monitoring information on another monitored person who is different from the certain monitored person is received, the display of the monitoring information display screen expressing the monitoring information on the certain
(Continued)

monitored person is continued as long as a predetermined input manipulation has been accepted.

20 Claims, 9 Drawing Sheets

(51) Int. Cl.
*A61G 12/00* (2006.01)
*G08B 25/04* (2006.01)
*A61B 5/00* (2006.01)
*G06F 19/00* (2018.01)
*G16H 40/67* (2018.01)
*A61B 5/05* (2006.01)
*A61B 5/11* (2006.01)

(52) U.S. Cl.
CPC .......... *A61B 5/748* (2013.01); *A61B 5/7465* (2013.01); *A61G 12/00* (2013.01); *G06F 19/00* (2013.01); *G08B 21/0208* (2013.01); *G08B 25/04* (2013.01); *G16H 40/67* (2018.01); *A61B 5/0507* (2013.01); *A61B 5/1115* (2013.01); *A61B 5/1117* (2013.01); *A61B 2505/00* (2013.01); *A61B 2562/08* (2013.01); *A61G 2203/20* (2013.01)

(58) Field of Classification Search
USPC ...................................... 340/870.4
See application file for complete search history.

(56) References Cited

U.S. PATENT DOCUMENTS

| | | | | |
|---|---|---|---|---|
| 2005/0261829 | A1* | 11/2005 | Furukawa ............ | G01C 21/367 701/414 |
| 2005/0266793 | A1* | 12/2005 | Grossman ......... | G06F 17/30017 455/3.01 |
| 2008/0309762 | A1* | 12/2008 | Howard .............. | G07C 5/0891 348/148 |
| 2011/0309938 | A1* | 12/2011 | Olsen .................... | F25D 29/008 340/584 |
| 2013/0018788 | A1* | 1/2013 | Johnson ................ | G07F 19/201 705/43 |

OTHER PUBLICATIONS

International Patent Application No. PCT/JP2016/056475; Int'l Written Opinion and the Search Report; dated May 17, 2016; 6 pages.

* cited by examiner

FIG. 3A ~ MT

| SENSING ID 4231 | DETERMINATION RESULT 4232 | DETERMINATION TIME (RECEPTION TIME) 4233 | STILL IMAGE (FILE NAME) 4234 | MOVING IMAGE (IP ADDRESS) 4235 | ACTION 4236 |
|---|---|---|---|---|---|
| SU-1 | SIT UP | 06:32 | SP1 | ... | 0 |
| SU-1 | LEAVE BED | 06:45 | SP2 | ... | 0 |
| ... | ... | ... | ... | ... | ... |
| ... | ... | ... | ... | ... | ... |

FIG. 3B ~ DT

| SENSING ID 4241 | INSTALLATION PLACE 4242 | MONITORED PERSON'S NAME 4243 |
|---|---|---|
| SU-1 | 101 | M-KAWA K-KO |
| SU-2 | 102 | K-YAMA M-TA |
| SU-3 | 103 | K-DA M-O |
| ... | ... | ... |
| ... | ... | ... |

DISPLAY DEVICE AND DISPLAY METHOD FOR MONITORED-PERSON MONITORING SYSTEM, AND MONITORED-PERSON MONITORING SYSTEM

TECHNICAL FIELD

The present invention relates to a display device and a display method for a monitored-person monitoring system in which a monitored person as a monitoring target to be monitored is monitored and predetermined information on the monitored person is transmitted to a reception device, and the monitored-person monitoring system.

BACKGROUND ART

Our country (Japan) has experienced an ageing society with the improvements of living standard, hygienic environment, medical level, and the like based on the high economic growth after the World War II, and more specifically the society's aging rate, which is the proportion of a society's population that is comprised of persons aged 65 or older among the total population, is over 21%, that is, now Japan is experiencing the super-ageing society. Among the total population of about 127.65 million, about 25.56 million are people aged 65 or older in 2005; on the other hand, in 2020, the number is expected to increase to about 34.56 million among the total population of about 124.11 million. In such an ageing society, people who require nursing or care because of the disease, injury, old age, or the like (people who require nursing, etc.) are expected to increase more than people who require nursing, etc. that would appear in the ordinary, no-ageing society. In addition, our country has suffered from the declining birth rate: for example, the total fertility rate in 2013 is as low as 1.43. This has recently resulted in situations that an elderly person who requires nursing, etc. is taken care of by an elderly member of his family (spouse, child, or sibling).

People who require nursing, etc. live in the hospital, the welfare facility for the elderly, or other facilities (in the Japanese law, such facilities are called the short-term in-patient facility for the elderly, the nursing home for the elderly, or the intensive care home for the elderly) where they live while they are nursed or taken care of. In those facilities, it may happen that the person who requires nursing, etc. hurts because of falling from the bed or falling on the ground while he is walking, or he sneaks out of the bed and walks around. Such situations need to be handled as quickly as possible. If these situations are left unresolved, more serious problems may occur. Therefore, in those facilities, nurses, caregivers, and other staff patrol on the regular basis to confirm safety states of people who require care.

However, people who require nursing, etc. have increased more than nurses, etc. and the nursing industry and the caregiving industry have chronically suffered from a shortage of workers. Moreover, fewer nurses, caregivers, and other staff work in the evening and the nighttime than in the daytime. Therefore, in the evening and the nighttime, the workload per person increases and the reduction of workload has been requested. The problem of the lack of young people who take care of elderlies as described above also occurs in the facilities, and sometimes old nurses, etc. take care of the elderlies. As getting older, we lose our power and even if we are healthy, we feel more burdened than young nurses and caregivers do, and we tend to need time to make a move or decision.

To deal with such a lack of workers and reduce the burden on the nurses and the caregivers, the technique to support the nursing work and the caring work has been demanded. In view of this, in recent years, the technique for monitoring a monitored person as a monitoring target to be monitored such as a person who requires nursing, etc. has been researched and developed.

One of the techniques made in view of the above is the nurse call system disclosed in Patent Literature 1. The nurse call system according to this Patent Literature 1 includes a calling slave device installed at a bed for a patient to call a nurse, and a calling master device installed at a nurse station for a nurse to respond to the calling from the calling slave device. This system includes a camera for taking a picture of the patient on the bed from above the bed, and a state determining means that determines the occurrence of at least one of a state in which the patient has sat up in bed and a state in which the patient has left the bed on the basis of the footage of the camera, and outputs an attentional state occurrence signal. The calling master device includes a notifying means that performs a notification operation upon accepting the attentional state occurrence signal.

On the other hand, from the aspect of the confirmation of safety, people who live alone are also the persons to be monitored just like people who require care as described above.

Incidentally, the monitored-person monitoring system monitors a plurality of monitored persons and therefore, a display device that displays the monitoring information on the monitored persons may need to display a plurality of pieces of monitoring information. In such a case, for example, when the display device displays a plurality of pieces of monitoring information on the display screen, too many pieces of information are displayed and it becomes difficult for a monitoring person to determine how to take action in accordance with the monitoring information.

CITATION LIST

Patent Literature

Patent Literature 1: JP 2014-90913 A

SUMMARY OF INVENTION

The present invention has been made in view of the above circumstances, and an object thereof is to provide a display device and a display method for a monitored-person monitoring system, which can display a plurality of pieces of monitoring information as appropriate and makes it easier to determine how to deal with the situation in accordance with the monitoring information, and the monitored-person monitoring system.

In regard to a display device and a display method for a monitored-person monitoring system according to the present invention, the device for a monitored-person monitoring system in which each of a plurality of monitored persons is sensed and the plurality of monitored persons is monitored receives and displays the monitoring information on the monitored person. While a monitoring information display screen expressing the monitoring information on a certain monitored person among the plurality of monitored persons is displayed, even if the monitoring information on another monitored person who is different from the certain monitored person is received, the display of the monitoring information display screen expressing the monitoring information on the certain monitored person is continued as long as a predetermined input manipulation has been accepted. A monitored-person monitoring system according to the present invention includes such a display device. Therefore, the display device and the display method for a monitored-person monitoring system according to the present invention and the monitored-person monitoring system according to the present invention can display a plurality of pieces of monitoring information as appropriate and it becomes easier to determine how to deal with the situation in accordance with the monitoring information.

Other object, feature, and advantage of the present invention and the aforementioned ones will be made apparent from the detailed description below and the attached drawings.

BRIEF DESCRIPTION OF DRAWINGS

FIG. 3 illustrates each structure of a sensing unit information table and a monitoring information table stored in the mobile terminal unit.

DESCRIPTION OF EMBODIMENTS

Figure 1:
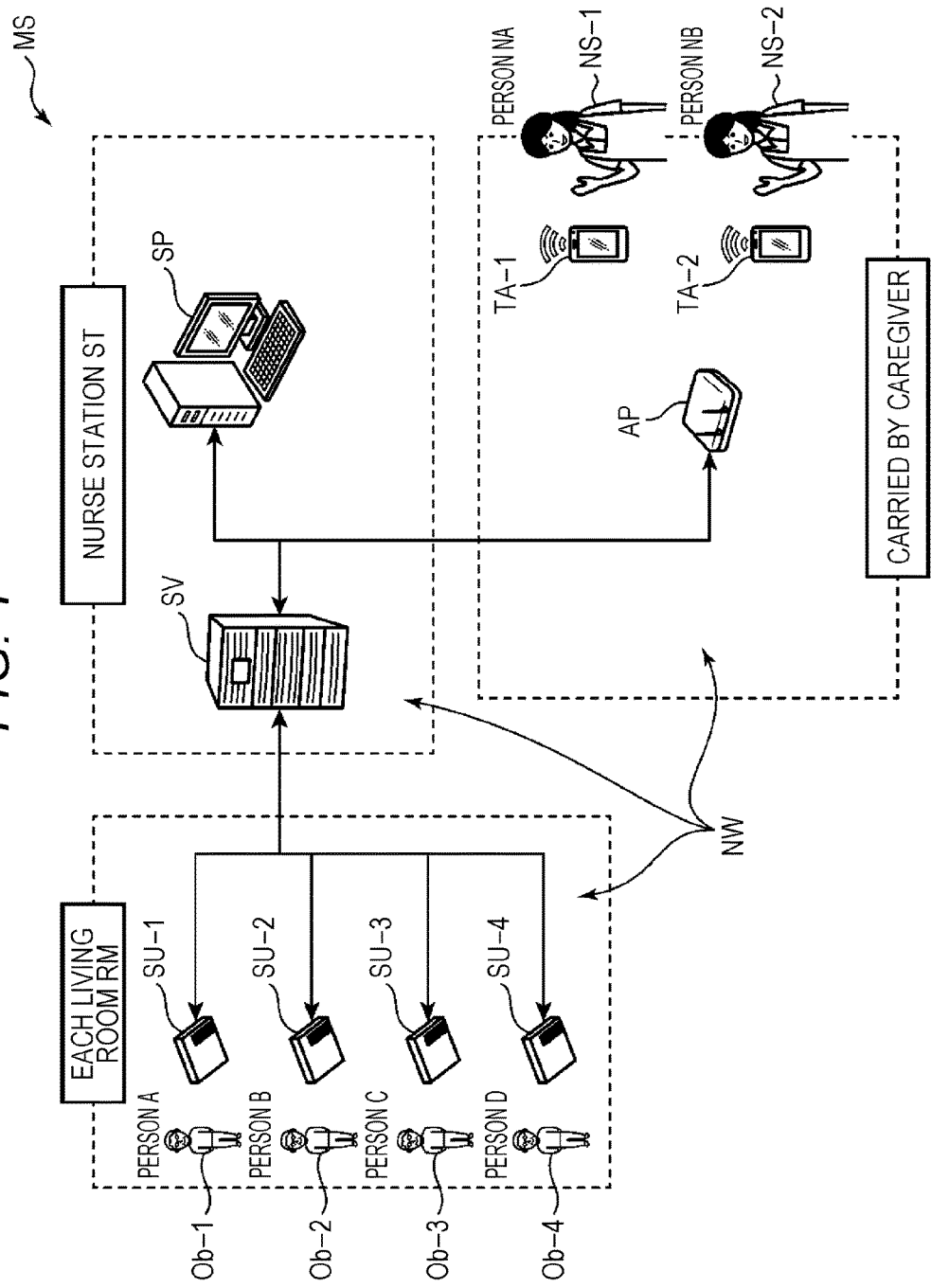
FIG. 1 illustrates a structure of a monitored-person monitoring system according to an embodiment.

One embodiment according to the present invention is hereinafter described on the basis of the drawings. Throughout the drawings, the same structure is denoted by the same reference sign and the description to the same structure will not be repeated. In the present specification, the structures that are collectively referred to are denoted by the reference sign without a suffix, and the structures that are individually referred to are denoted by the reference sign with a suffix.

The present monitored-person monitoring system is to sense each of a plurality of monitored persons (persons to be watched) Ob, which corresponds to monitoring targets (watching targets) to be monitored (watched), and monitor the plurality of monitored persons Ob. A display device used for this monitored-person monitoring system is a device that receives the monitoring information on the monitored person Ob and displays the received monitoring information. While a monitoring information display screen SC-A expressing the monitoring information on a certain monitored person Ob-A among the plurality of monitored persons Ob is displayed, even if the monitoring information on another monitored person Ob-B, who is different from the certain monitored person Ob-A, among the plurality of monitored persons Ob is received, the display of the monitoring information display screen SC-A expressing the monitoring information on the certain monitored person Ob-A is continued as long as a predetermined input manipulation has been accepted. In the present embodiment, the display device displays a different monitoring information reception display expressing the reception of the monitoring information on the other monitored person Ob-B on the monitoring information display screen SC-A expressing the monitoring information on the certain monitored person Ob-A. In the present embodiment, if there is second monitoring information MI-t1 at a time t1 before first monitoring information MI-t2 corresponding to a monitoring information display screen SC-t2 that is currently displayed, the display device displays a first different monitoring information reception display expressing the reception of the second monitoring information MI-t1 on one end of the monitoring information display screen SC-t2 that is currently displayed, and if there is third monitoring information MI-t3 at a time t3 after the first monitoring information MI-t2 corresponding to the monitoring information display screen SC-t2 that is currently displayed, the display device displays a second different monitoring information reception display expressing the reception of the third monitoring information MI-t3 on the other end of the monitoring information display screen SC-t2 that is currently displayed. In the present embodiment, upon accepting a predetermined second input manipulation (for example, flick, tap, or move the whole display device), which is different from the aforementioned predetermined input manipulation, the display device shifts the display from the monitoring information display screen SC-t2 that is currently displayed to the monitoring information display screen SC expressing the monitoring information MI corresponding to the different monitoring information reception display in accordance with the second input manipulation. For example, by the flick, the monitoring information display screen expressing the monitoring information corresponding to the different monitoring information reception display displayed in the flick destination is preferably displayed. In another example, by the tap, the monitoring information display screen expressing the monitoring information corresponding to the different monitoring information reception display displayed in the tapped position is displayed. In still another example, by moving the whole display device, the monitoring information display screen expressing the monitoring information corresponding to the different monitoring information reception display displayed in the moving destination is displayed. Note that at least one of flick, tap, and moving the whole display device may be the second predetermined input manipulation described above. In the present embodiment, the display device has, in the chronological order, the monitoring information display screen SC-A expressing the monitoring information on the certain monitored person Ob-A and the other monitoring information display screen SC-B expressing the monitoring information on the other monitored person Ob-B. While the monitoring information display screen SC-A expressing the monitoring information on the certain monitored person Ob-A is displayed, if the monitoring information on the other monitored person Ob-B is received and the predetermined input manipulation has not been accepted, the monitoring information display screen SC-A expressing the monitoring information on the certain monitored person Ob-A is shifted to the other monitoring information display screen SC-B expressing the monitoring information on the other monitored person Ob-B and displayed.

Figure 2:
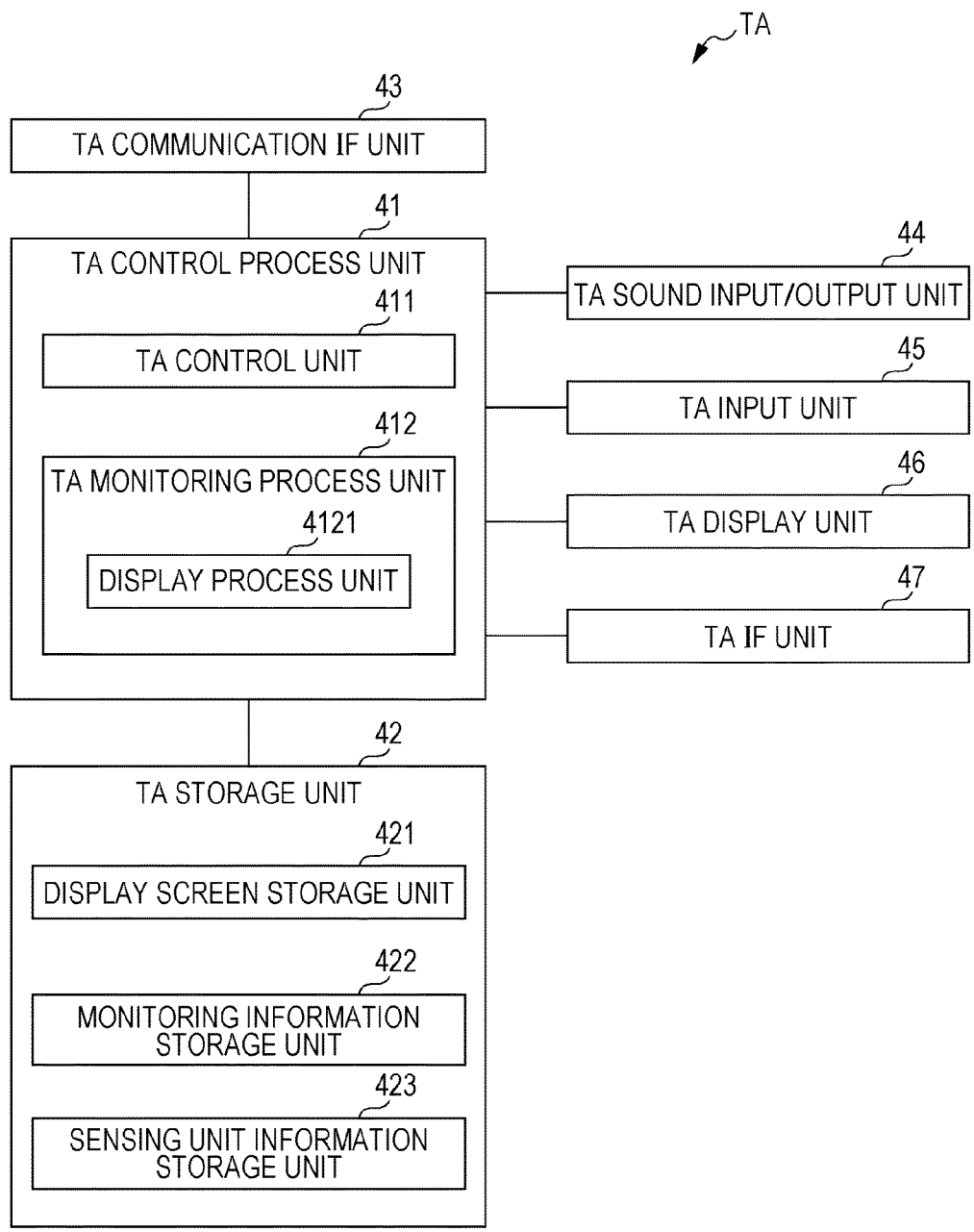
FIG. 2 illustrates a structure of a mobile terminal unit in the monitored-person monitoring system according to the embodiment.

FIG. 1 illustrates a structure of the monitored-person monitoring system according to the embodiment. FIG. 2 illustrates a structure of the mobile terminal unit in the monitored-person monitoring system according to the embodiment. FIG. 3 illustrates each structure of a sensing unit information table and a monitoring information table stored in the mobile terminal unit. FIG. 3A expresses the monitoring information table, and FIG. 3B expresses the sensing unit information table.

Such a monitored-person monitoring system MS includes, as illustrated in FIG. 1: a plurality of sensing units (sensor units) SU (SU-1 to SU-4); a management server unit SV; a fixed terminal unit SP; and one or a plurality of mobile terminal units TA (TA-1, TA-2). These are connected with or without a wire so that communication therebetween is possible through a Local Area Network (LAN), or another network (network, communication network) NW such as a telephone network or a data communication network. The network NW may include a relay device for relaying communication signals, such as a repeater, a bridge, a rooter, or a cross connect. In the example illustrated in FIG. 1, these plural sensing units SU-1 to SU-4, the management server unit SV, the fixed terminal unit SP, and the plurality of mobile terminal units TA-1 and TA-2 are connected so that the communication therebetween is possible through the wireless LAN (for example, IEEE 802.11-compliant LAN) NW including the access point AP.

The monitored-person monitoring system MS is installed at an appropriate position in accordance with the monitored person Ob. The monitored person (person to be watched) Ob is, for example, a person who needs the nursing care because of disease, injury, or the like, a person who needs care due to the decline in physical ability, or a person who lives alone. In particular, since the early detection and the quick response are possible, the monitored person Ob is preferably the person who needs to be found in the occurrence of a predetermined inconvenience such as an abnormality. Therefore, the monitored-person monitoring system MS is suitably installed in the building such as the hospital, the welfare facility for the elderly, or the dwelling unit in accordance with the type of monitored person Ob. In the example illustrated in FIG. 1, the monitored-person monitoring system MS is installed in the building of the nursing care facility including a plurality of rooms such as living rooms RM where a plurality of monitored persons Ob live and a nurse station ST.

The sensing unit SU has a communication function of communicating with other units SV, SP, and TA through the network NW, takes a picture of the monitored person Ob to generate an image, and senses the monitored person Ob from the generated image. More specifically, the sensing unit SU includes, for example: a communication interface circuit (for example, LAN card or the like) for communicating with other units SV, SP, and TA through the network; a Doppler shift type body motion sensor which senses the monitored person Ob by transmitting and receiving a microwave and detecting a Doppler shift of the microwave generated by the body motion of the monitored person Ob (for example, aspiration or the like); an image sensor which takes a picture of the monitored person Ob to generate an image; a data process circuit which determines the state (status) of the monitored person Ob as a result of sensing the monitored person Ob on the basis of the output of the body motion sensor (body motion sensor output) and the output of the image sensor (image); a control circuit which controls these; and a peripheral circuit for those above. The sensing result is transmitted to the management server unit SV. The sensing unit SU transmits the generated image (including a still image and a moving image) to the predetermined other units SV, SP, and TA. In the present embodiment, moreover, the sensing unit SU includes a nurse call circuit which notifies the nurse call to the fixed terminal unit SP, the mobile terminal unit TA, or the like, and a speaking circuit which enables the voice call with the fixed terminal unit SP, the mobile terminal unit TA, or the like, and thus the nurse call and the voice call are possible. As one example, FIG. 1 illustrates four sensing units: first to fourth sensing units SU-1 to SU-4. The first sensing unit SU-1 is installed in a living room RM-1 (not shown) of a person A Ob-1, one of the monitored persons Ob. The second sensing unit SU-2 is installed in a living room RM-2 (not shown) of a person B Ob-2, one of the monitored persons Ob. The third sensing unit SU-3 is installed in a living room RM-3 (not shown) of a person C Ob-3, one of the monitored persons Ob. The fourth sensing unit SU-4 is installed in a living room RM-4 (not shown) of a person D Ob-4, one of the monitored persons Ob.

The management server unit SV is equipment which has a communication function of communicating with other units SU, TA, and SP through the network NW, receives the sensing result on the monitored person Ob and the image of the monitored person Ob from the sensing unit SU, and manages the information (monitoring information) related to the monitoring of the monitored person Ob. Upon receiving the sensing result on the monitored person Ob and the image of the monitored person Ob from the sensing unit SU, the management server unit SV transmits the communication signal (monitoring information communication signal) containing the monitoring information related to the monitoring of the monitored person Ob to the fixed terminal unit SP and the mobile terminal unit TA. The management server unit SV provides a client (in this embodiment, the fixed terminal unit SP, the mobile terminal unit TA, or the like) with the data that satisfies the demand of the client. Such a management server unit SV can be structured by, for example, a computer having a communication function.

The fixed terminal unit SP has a communication function of communicating with other units SU, SV, and TA through the network NW, a display function of displaying predetermined information, an input function of inputting a predetermined instruction or data, and the like. The fixed terminal unit SP functions as a user interface (UI) of the monitored-person monitoring system MS by the input of a predetermined instruction or data, which are to be transmitted to the management server unit SV or the mobile terminal unit TA or by the display of the sensing result or the image obtained in the sensing unit SU, for example. Such a fixed terminal unit SP can be structured by, for example, a computer having a communication function.

The mobile terminal unit TA has a communication function of communicating with other units SV, SP, and SU through the network NW, a display function of displaying predetermined information, an input function of inputting a predetermined instruction or data, a calling function of making a voice call, and the like. By inputting a predetermined instruction or data, which are to be transmitted to the management server unit SV or the sensing unit SU or displaying the sensing result or the image obtained in the sensing unit SU by the notification from the management server unit SV, for example, the mobile terminal unit TA receives and displays the monitoring information related to the monitoring of the monitored person Ob.

The management server unit SV may correspond to one example of the display device and function as the display device, and the fixed terminal unit SP may correspond to one example of the display device and function as the display device. Here, description is made of the case in which the mobile terminal unit TA corresponds to one example of the display device and functions as the display device. Note that if the management server unit SV corresponds to one example of the display device and functions as the display device, the management server unit SV can be structured in the same manner as described below. Moreover, if the fixed terminal unit SP corresponds to one example of the display device and functions as the display device, the fixed terminal unit SP can be similarly structured in the same manner as described below.

In the present embodiment, such a mobile terminal unit TA includes the following, for example: a terminal control process unit (TA control process unit) 41; a terminal storage unit (TA storage unit) 42; a terminal communication interface unit (TA communication IF unit) 43; a terminal sound input/output unit (TA sound input/output unit) 44; a terminal input unit (TA input unit) 45; a terminal display unit (TA display unit) 46; and a terminal interface unit (TA IF unit) 47 as illustrated in FIG. 2.

The TA sound input/output unit 44 is a device which is connected to the TA control process unit 41, obtains an external sound, and inputs the sound to the mobile terminal unit TA, and a device which generates and outputs a sound according to electric signals expressing the sound in accordance with the control of the TA control process unit 41. The TA sound input/output unit 44 includes, for example, a microphone which converts the acoustic vibration of the sound into electric signals, or the like, and a speaker which converts the electric signals of the sound into the acoustic vibration, or the like. The TA sound input/output unit 44 outputs the electric signals expressing the external sound to the TA control process unit 44, converts the electric signals input from the TA control process unit 44 into the acoustic vibration, and outputs the acoustic vibration.

The TA input unit 45 is a device which is connected to the TA control process unit 41, for example, accepts a predetermined manipulation, and performs the input to the mobile terminal unit TA, and corresponds to, for example, a plurality of input switches to each of which a predetermined function is assigned. Examples of the predetermined manipulation include the manipulation of inputting the log-in ID, the input manipulation as to whether to take action, for example, nurse the monitored person Ob whose sensing result or image has been notified, the input manipulation for inputting to the mobile terminal unit TA the information expressing that the user is currently considering (making decision) whether to take action for the monitored person, and other manipulations necessary in the monitoring. The TA display unit 46 is a display device which is connected to the TA control process unit 41 and displays a predetermined manipulation content input through the TA input unit 45, the monitoring information related to the monitoring of the monitored person Ob who is monitored by the monitored-person monitoring system MS (such as the state or the image of the determined monitored person Ob), and the like in accordance with the control of the TA control process unit 41, and corresponds to, for example, an LCD, an organic EL display, or the like. In the present embodiment, the TA input unit 45 and the TA display unit 46 constitute a touch panel. In this case, the TA input unit 45 is a position input device which detects and inputs the manipulation position by, for example, a resistance film method or an electrostatic capacitive method. In this touch panel, the position input device is provided on a display surface of the TA display unit 46, and one or a plurality of input content candidates that can be input is displayed in the TA display unit 46. For example, when a user such as a nurse, a caregiver, or other staff (a person who monitors) touches the display position where the input content that the user wants to input is displayed, the position input device detects the touched position and the display content displayed at the detected position is input to the mobile terminal unit TA as the user's manipulation input content.

The TA IF unit 47 is a device which is connected to the TA control process unit 41, and exchanges the data with an external device in accordance with the control of the TA control process unit 41, and corresponds to, for example, an interface circuit compatible to Bluetooth (registered trademark) specification, an interface circuit performing infrared communication in accordance with Infrared Data Association (IrDA) specification or the like, an interface circuit compatible to Universal Serial Bus (USB) specification, or the like.

The TA communication IF unit 43 is a communication device which is connected to the TA control process unit 41 and performs communication in accordance with the control of the TA control process unit 41. The TA communication IF unit 43 generates a communication signal containing data to be transferred that is input from the TA control process unit 41, in accordance with the communication protocol used in the network NW of the monitored-person monitoring system MS, and transmits the generated communication signal to other units SU, SV, and SP through the network NW. The TA communication IF unit 43 receives the communication signal from the other units SU, SV, and SP through the network NW, extracts data from the received communication signal, converts the extracted data into the data in format that the TA control process unit 41 can process, and outputs the converted data to the TA control process unit 41.

The TA storage unit 42 is a circuit which is connected to the TA control process unit 41 and stores various kinds of predetermined programs and various kinds of predetermined data in accordance with the control of the TA control process unit 41. The various kinds of predetermined programs include, for example, control process programs such as monitoring process programs for processing the monitoring information related to the monitoring of the monitored person Ob. The monitoring process programs include, for example, a display process program for processing the operation related to the display of the monitoring information. The various kinds of predetermined data include various pieces of data such as the monitoring information related to the monitoring of the monitored person Ob and the sensing unit information on the sensing unit SU. The TA storage unit 42 includes, for example, a read only memory (ROM) corresponding to a nonvolatile storage element, an electrically erasable programmable read only memory (EEPROM) corresponding to a nonvolatile storage element that cannot be rewritten, or the like. The TA storage unit 42 includes a random access memory (RAM) or the like. The RAM serves as a working memory of the TA control process unit 41 for storing, for example, the data formed in the execution of the predetermined program. Then, the TA storage unit 42 functionally includes a display screen storage unit 421, a monitoring information storage unit 422, and a sensing unit information storage unit 423.

The display screen storage unit 421 stores the image such as the display screen to be displayed in the TA display unit 46 in accordance with the control of a display process unit 4121 to be described below in the TA control process unit 41, and corresponds to, for example, a video memory (VRAM) or the like. If there is a plurality of monitoring information screens to be described below expressing the pieces of monitoring information on each of the plurality of monitored persons Ob, the display screen storage unit 421 stores these plural monitoring information screens while associating these screens with each other in the chronological order. These plural monitoring information screens which are associated with each other in the chronological order may be displayed in the TA display unit 46 by changing the screen from one monitoring information screen to another monitoring information screen selectively in response to the input manipulation accepted in the TA input unit 45, or may be displayed in the TA display unit 46 by shifting the screen from one monitoring information screen to another monitoring information screen while these screens are displayed continuously in response to the input manipulation accepted in the TA input unit 45. In the present embodiment, more specifically, when a plurality of monitoring information communication signals containing the plurality of pieces of monitoring information on each of the plurality of different monitored persons Ob is received, the plurality of monitoring information screens for each of the plurality of monitoring information communication signals is connected in the chronological order and formed planarly. More specifically, if the plurality of monitoring information screens is displayed in the TA display unit 46 in the present embodiment, for example, the screens are connected in the chronological order in the up-down direction and formed planarly. The up-down direction may be a left-right direction instead. The chronological order may be the order based on, for example, the reception time of the monitoring information communication signal or the order based on the determination time. The plane size stored in the display screen storage unit 421 is substantially the same as the size of the screen display region of the TA display unit 46 usually; however, when the plurality of monitoring information communication signals is received, the monitoring information screen to display the monitoring information contained in one monitoring information communication signal is formed in the usual plane size and the plurality of monitoring information screens for the plurality of monitoring information communication signals is connected in the chronological order and formed planarly. Therefore, the plane size in the case where the plurality of monitoring information communication signals is received is the size according to the number of monitoring information screens. Of the plurality of monitoring information screens formed in this plane, only the part with the size of the screen display region of the TA display unit 46 is displayed by the display process unit 4121 in the TA display unit 46 in response to the input manipulation accepted in the TA input unit 45.

The monitoring information storage unit 422 is to store the monitoring information related to the monitoring of the monitored person Ob. The monitoring information includes: a sensing unit identifier (sensing ID) for specifying and identifying the sensing unit SU; information expressing the determination result determined as the state of the monitored person Ob by the sensing unit SU which is related to the sensing ID and has the sensing ID (in this embodiment, the determination result information including sitting up in bed, leaving bed, falling down, and minute abnormal body motion); information expressing the time when the sensing unit SU which is related to the sensing ID and has the sensing ID determines the state of the monitored person Ob (determination time information); a still image of the monitored person Ob used when the sensing unit SU which is related to the sensing ID and has the sensing ID determines the state of the monitored person Ob (if a plurality of images is used in the determination, one of those images (for example, the last image)); a communication address of the sensing unit SU which is related to the sensing ID and has the sensing ID (for example, the IP address or the like); and the action information expressing whether the intention to take action for the monitored person Ob monitored by the sensing unit SU which is related to the sensing ID and has the sensing ID, for example, to save his life, nurse, help, or assist the monitored person Ob has been input to the mobile terminal unit TA. Note that instead of the determination time, the reception time of the communication signal at which the determination result and the notification of the image are received may be used.

This monitoring information is stored in the monitoring information storage unit 422 in the table format in this embodiment. The monitoring information table MT in which this monitoring information is registered includes, for example, the following as illustrated in FIG. 3A: a sensing ID field 4231 in which the sensing ID is registered; a determination result field 4232 in which the determination result information on the sensing unit SU with the sensing ID registered in the sensing ID field is registered; a determination time field 4233 in which the determination time information on the sensing unit SU with the sensing ID registered in the sensing ID field is registered; a still image field 4234 in which the still image on the sensing unit SU with the sensing ID registered in the sensing ID field is registered; a moving image field 4235 in which a communication address (for example, IP address or the like) of the sensing unit SU with the sensing ID registered in the sensing ID field is registered as the place from which the live moving image is acquired; and an action field 4236 in which the action information expressing whether the user has the intention to take action for the monitored person Ob monitored by the sensing unit SU with the sensing ID registered in the sensing ID field is registered. A record is formed every time the monitoring information communication signal is received. In the action field 4236, a flag representing the action information expressing whether the user has the intention to take action is registered. For example, in the present embodiment, in the action field 4236, the flag "1" representing that the intention to take action is input to the mobile terminal unit TA or the flag "0" representing that the intention to take action is not input to the mobile terminal unit TA is registered. Note that in the still image field 4234, for example, the image data of the still image may be registered or, for example, the file name of the image data of the still image may be registered. In the first record in the example illustrated in FIG. 3A, "SU-1" is registered in the sensing ID field 4231, "sit up in bed" is registered in the determination result field 4232, "06:32" is registered in the determination time field 4233, "SP1" is registered in the still image field 4234, "..." ( is an integer value) is registered in the moving image field 4235, and "0" is registered in the action field 4236. In the second record, "SU-1" is registered in the sensing ID field 4231, "leave bed" is registered in the determination result field 4232, "06:45" is registered in the determination time field 4233, "SP2" is registered in the still image field 4234, "..." ( is an integer value) is registered in the moving image field 4235, and "0" is registered in the action field 4236.

In the example illustrated in FIG. 3A, the monitoring information table MT includes the moving image field 4235 but the moving image field 4235 may be omitted from the monitoring information table MT illustrated in FIG. 3A if a table expressing the relation between the sensing ID and the communication address of the sensing unit SU as the place from which the live moving image is acquired is prepared separately from the monitoring information table MT and stored in the monitoring information storage unit 422.

The sensing unit information storage unit 423 stores the sensing unit information on the sensing unit SU. The sensing unit information includes the place where the sensing unit SU is installed and the name of a monitored person who is monitored by the sensing unit SU. This sensing unit information is stored in the sensing unit information storage unit 423 in the table format in the present embodiment. The sensing unit information table DT in which the sensing unit information is registered includes, for example, as illustrated in FIG. 3B: a sensing ID field 4241 in which the sensing ID is registered; an installation place field 4242 in which the installation place of the sensing unit SU which is related to the sensing ID and has the sensing ID is registered, and a monitored-person name field 4243 in which the name of the monitored person Ob who is monitored by the sensing unit SU which is related to the sensing ID and has the sensing ID is registered, and a record is provided for each sensing ID. In the example illustrated in FIG. 3B, in the first record, "SU-1" is registered in the sensing ID field 4241, "101" is registered in the installation place field 4242, and "M-kawa K-ko" is registered in the monitored-person name field 4243, and in the second record, "SU-2" is registered in the sensing ID field 4241, "102" is registered in the installation place field 4242, and "K-yama M-ta" is registered in the monitored-person name field 4243.

The TA control process unit 41 is a circuit which controls each part of the mobile terminal unit TA in accordance with the function of that part, and processes the monitoring information related to the monitoring of the monitored person Ob. The TA control process unit 41 includes, for example, a central processing unit (CPU) and its peripheral circuit. The TA control process unit 41 functionally has a terminal control unit (TA control unit) 411 and a terminal monitoring process unit (TA monitoring process unit) 412 by executing control process programs, and the TA monitoring process unit 412 functionally has the display process unit 4121.

The TA control unit 411 controls each part of the mobile terminal unit TA in accordance with the function of that part, thereby controlling the entire mobile terminal unit TA.

The TA monitoring process unit 412 processes the monitoring information related to the monitoring of the monitored person Ob. More specifically, when the TA communication IF unit 43 has received the monitoring information communication signal, the TA monitoring process unit 412 registers the monitoring information on the monitored person Ob contained in the received monitoring information communication signal in the monitoring information table MT so that the monitoring information is stored in the TA monitoring information storage unit 422.

The display process unit 4121 is to process the operation related to the display of the monitoring information. More specifically, for example, while a monitoring information screen 52-A expressing the monitoring information on the certain monitored person Ob-A among a plurality of different monitored persons Ob is displayed, even if the monitoring information communication signal containing the monitoring information on the other monitored person Ob-B, who is different from the certain monitored person Ob-A, among the plurality of monitored persons Ob is received, the display process unit 4121 continues the display of the monitoring information screen 52-A expressing the monitoring information on the certain monitored person Ob-A as long as a predetermined input manipulation (for example, "tap" or the like) has been accepted in the TA input unit 45.

In the case where a plurality of monitoring information communication signals containing each of the monitoring information on each of the plurality of different plural monitored persons Ob is received and there is the plurality of monitoring information screens corresponding to each of the plurality of monitoring information communication signals, while the monitoring information screen 52-A expressing the monitoring information on the certain monitored person Ob-A is displayed, if the monitoring information on the other monitored person Ob-B is received and the predetermined input manipulation has not been accepted, the display process unit 4121 shifts the display from the monitoring information screen 52-A expressing the monitoring information on the certain monitored person Ob-A to the other monitoring information screen 52-B expressing the monitoring information on the other monitored person Ob-B.

For example, the display process unit 4121 displays, on the monitoring information screen 52-A expressing the monitoring information on the certain monitored person Ob-A, the different monitoring information reception display (for example, a stick-like display or the like) expressing the reception of the monitoring information on the other monitored person Ob-B.

In another example, the display process unit 4121 performs the following process: if there is the second monitoring information MI-t1 at the time before the first monitoring information MI-t2 corresponding to a first monitoring information screen 52-t2, the first monitoring information screen 52-t2 and a second monitoring information screen 52-t1 expressing the second monitoring information MI-t1 are stored in the display screen storage unit 421 while the first monitoring information screen 52-t2 and the second monitoring information screen 52-t1 are associated with each other in the chronological order; if there is the third monitoring information MI-t3 at the time after the first monitoring information MI-t2 corresponding to the first monitoring information screen 52-t2, the first monitoring information screen 52-t2 and a third monitoring information screen 52-t3 expressing the third monitoring information MI-t3 are stored in the display screen storage unit 421 while the first monitoring information screen 52-t2 and the third monitoring information screen 52-t3 are associated with each other in the chronological order; if there is the second monitoring information MI-t1 while the first monitoring information screen 52-t2 is displayed in the TA display unit 46, the display process unit 4121 displays a first different monitoring information reception display 531 expressing the reception of the second monitoring information MI-t1 at one end of the first monitoring information screen 52-t2; if there is the third monitoring information MI-t3 while the first monitoring information screen 52-t2 is displayed in the TA display unit 46, the display process unit 4121 displays a second different monitoring information reception display 531 expressing the reception of the third monitoring information MI-t3 at the other end of the first monitoring information screen 52-t2; and upon accepting the flick as an input manipulation different from the predetermined input manipulation in the TA input unit 45, the display of the first monitoring information screen 52-t2 is shifted to the display of the monitoring information screen 52 expressing the monitoring information corresponding to the different monitoring information reception display 531 displayed at the flick destination.

Such a mobile terminal unit TA can be structured by, for example, a tablet computer, a smart phone, or a mobile phone, or other portable communication terminal device.

Next, an operation of the present embodiment will be described. In the monitored-person monitoring system MS with such a structure, when the power is input to the units SU, SV, SP, and TA, the necessary units execute initialization and start the operation. In the mobile terminal unit TA, by executing the control process programs, the TA control unit 411 and the TA monitoring process unit 412 are functionally structured in the TA control process unit 41 and the display process unit 4121 is functionally structured in the TA monitoring process unit 412.

Then, the monitored-person monitoring system MS with the above structure monitors each monitored person Ob usually by the following operation: the sensing unit SU samples the output of the body motion sensor and the output of the image sensor at a predetermined sampling cycle and determines the state (status) of the monitored person Ob on the basis of the output of the body motion sensor and the output of the image sensor that are sampled; and when the result of determination indicates that the monitored person Ob is in a preset state (for example, in the present embodiment, sitting up in bed, leaving bed, falling down, and minute abnormal body motion, and the like), the communication signal (monitoring information communication signal) containing the sensing ID of the own unit, the determination result information expressing the determination result determined as the state of the monitored person Ob, the determination time information expressing the determination time, the image data of the still image of the monitored person Ob employed in the determination (if a plurality of images is used in the determination, one of them (for example, the last image)), the communication address of the own unit (for example, IP address) as the communication destination to which the moving image is downloaded, and the like are transmitted to the management server unit SV through the network NW. As the communication address of the own unit, the communication address of the transmission source contained in the header may also be employed. The sensing unit SU can determine the state (status) of the monitored person Ob by the known technique. For example, the sensing unit SU detects the body motion of the chest of the monitored person Ob with the aspiration (up-down movement of the chest) by the body motion sensor, and if sensing the disturbance in the cycle of the body motion of the chest or the amplitude of the body motion of the chest, which is less than or equal to a predetermined threshold, determines the body has moved abnormally. In addition, for example, the sensing unit SU obtains the image of the monitored person Ob by the image sensor, detects a human area of the monitored person Ob from the obtained image, determines the posture of the monitored person Ob from the aspect ratio of the detected human area (for example, the standing posture, the sitting posture, or the lying posture), detects the position of the detected human area, and determines whether the monitored person has sat up in bed, left bed, or fallen down on the basis of the posture and position of the monitored person Ob through the determination and detection as above.

Upon receiving the monitoring information communication signal from the sensing unit SU through the network NW, the management server unit SV stores (records) the sensing ID, the determination result information, the determination time information, the image data of the still image, and the communication address for obtaining the moving image that are contained in the monitoring information communication signal while associating these pieces of information with each other. The management server unit SV transmits the monitoring information communication signal to the fixed terminal unit SP and the mobile terminal unit TA by the simultaneous communication such as the broadcasting or multicasting. This notifies the state (status) of the monitored person Ob. If the communication address of the transmission source is also used as the communication address to obtain the moving image, the communication address of the transmission source becomes the communication address of the management server unit SV by the transfer of the monitoring information communication signal by the management server unit SV; therefore, the management server unit SV performs the simultaneous communication of the monitoring information communication signal after the communication address of the sensing unit SU of the transmission source contained in the header is contained in the payload of the monitoring information communication signal. The management server unit SV may transmit by unicasting, the monitoring information communication signal to the mobile terminal unit TA associated in advance with the sensing unit SU which has transmitted the monitoring information communication signal.

Upon receiving the monitoring information communication signal from the management server unit SV through the network NW, the fixed terminal unit SP and the mobile terminal unit TA display the monitoring information related to the monitoring of the monitored person Ob contained in the monitoring information communication signal. Detailed description will be made of the operation of displaying the monitoring information by the mobile terminal unit TA. By such an operation, the monitored-person monitoring system MS substantially senses each monitored person Ob and monitors the monitored person Ob with each sensing unit SU, the management server unit SV, the fixed terminal unit SP, and the mobile terminal unit TA.

Figure 4:
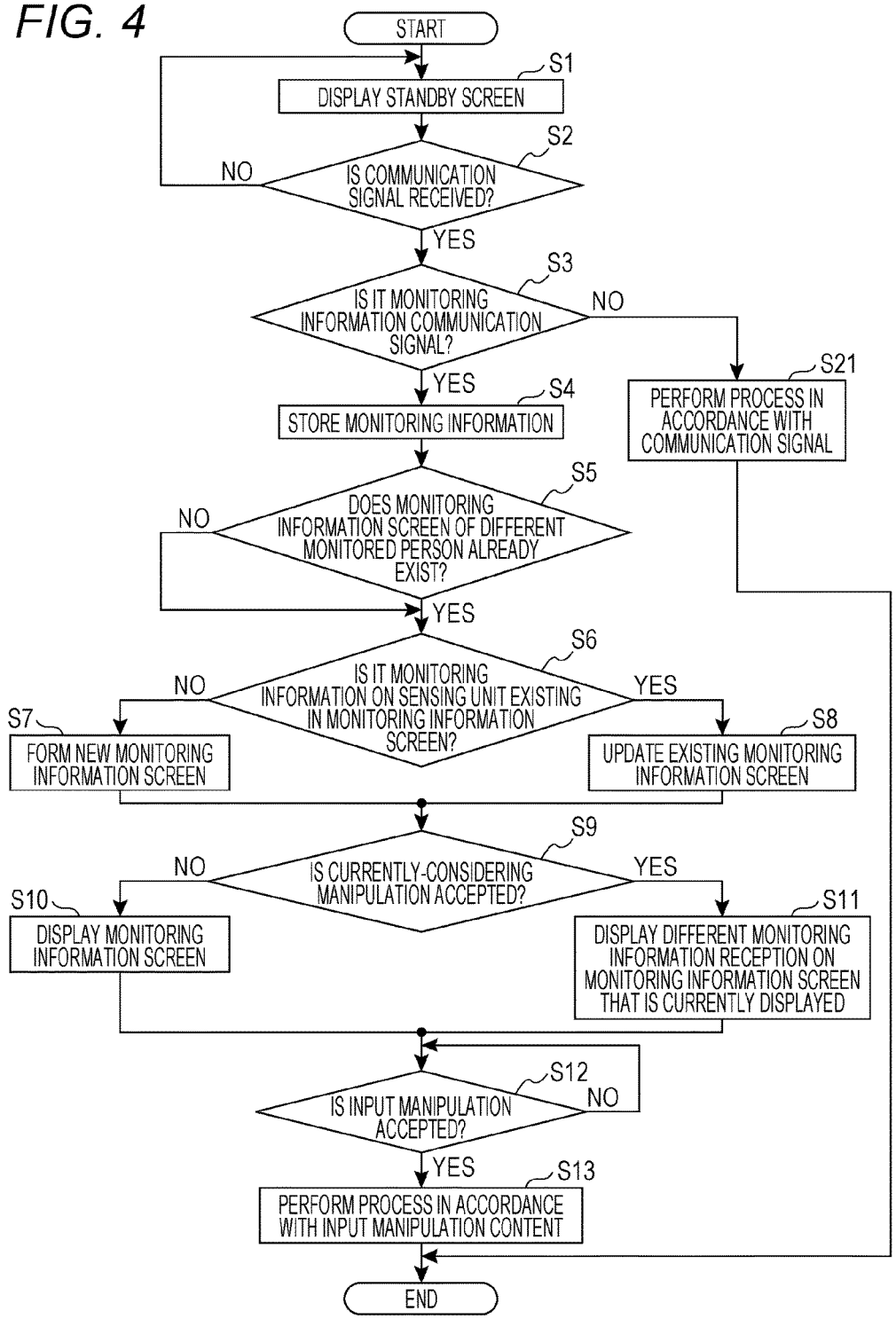
FIG. 4 is a flowchart of the operation related to the display of the monitoring information in the mobile terminal unit.
Figure 5:
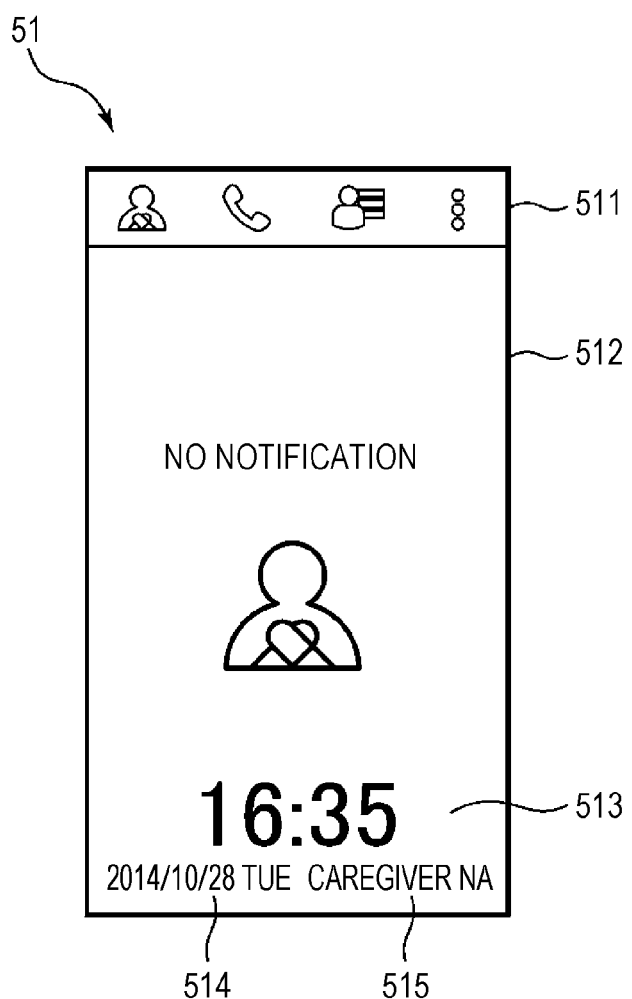
FIG. 5 illustrates one example of a standby screen displayed in the mobile terminal unit.
Figure 6:
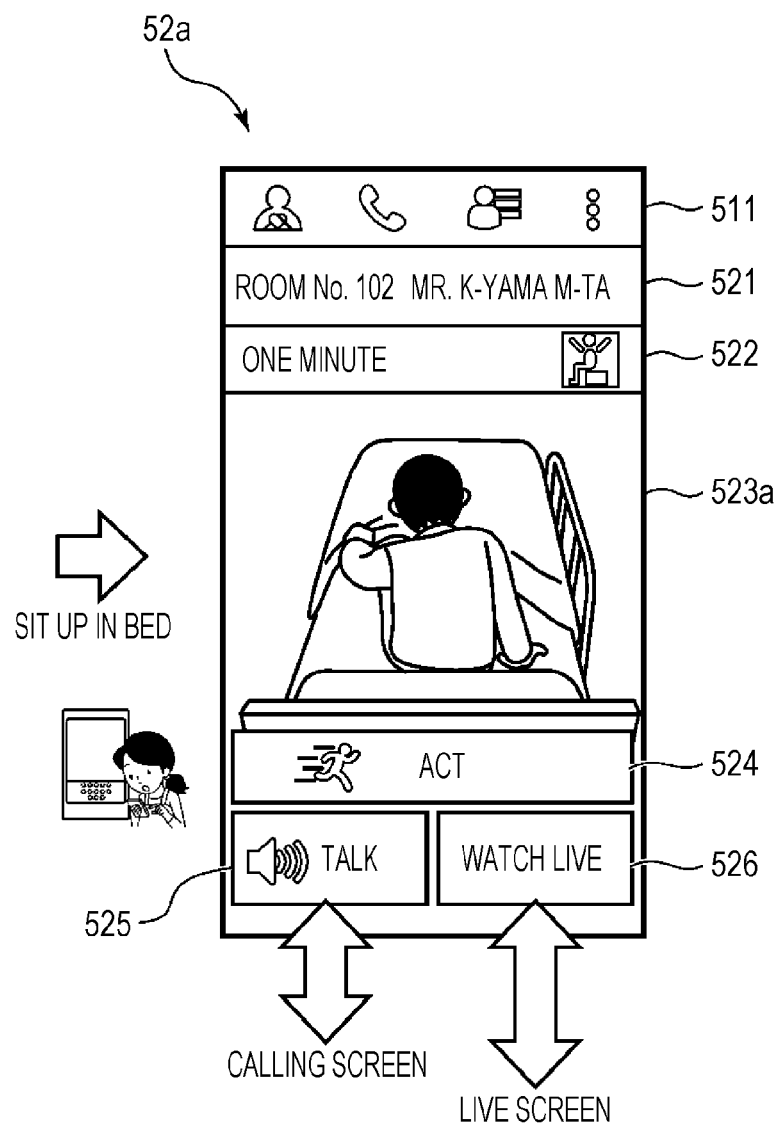
FIG. 6 illustrates one example of the monitoring information screen displayed in the mobile terminal unit having received the notification that the monitored person has sat up in bed.
Figure 7:
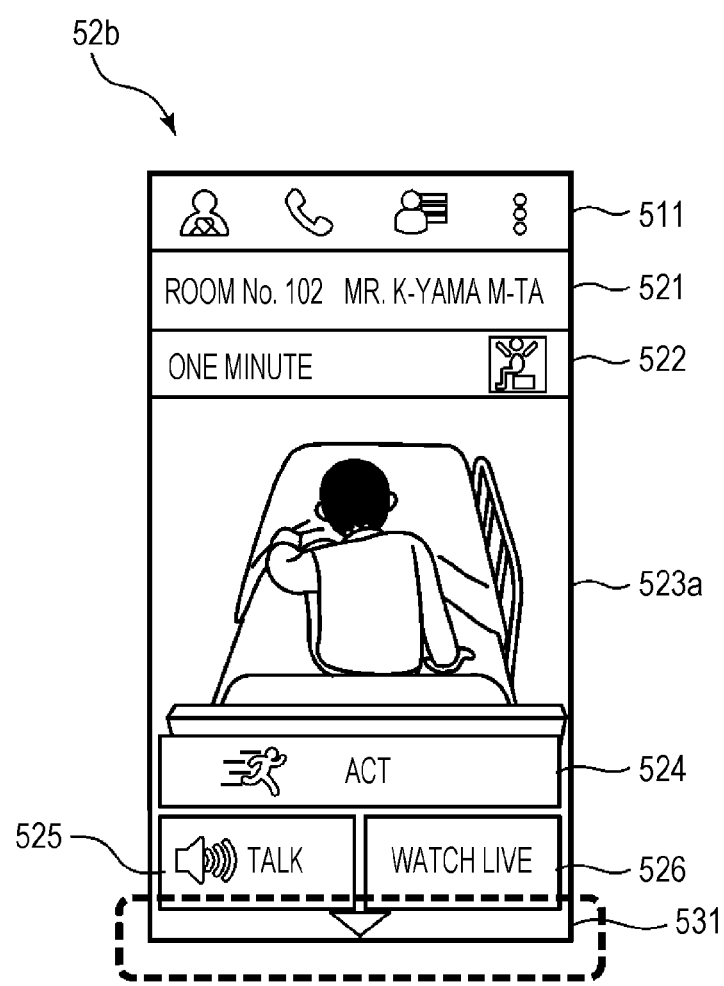
FIG. 7 illustrates one example of the monitoring information screen displayed in the mobile terminal unit having received the notification of the monitoring information on a monitored person who is different from the monitored person having already received the notification of the monitoring information.
Figure 8:
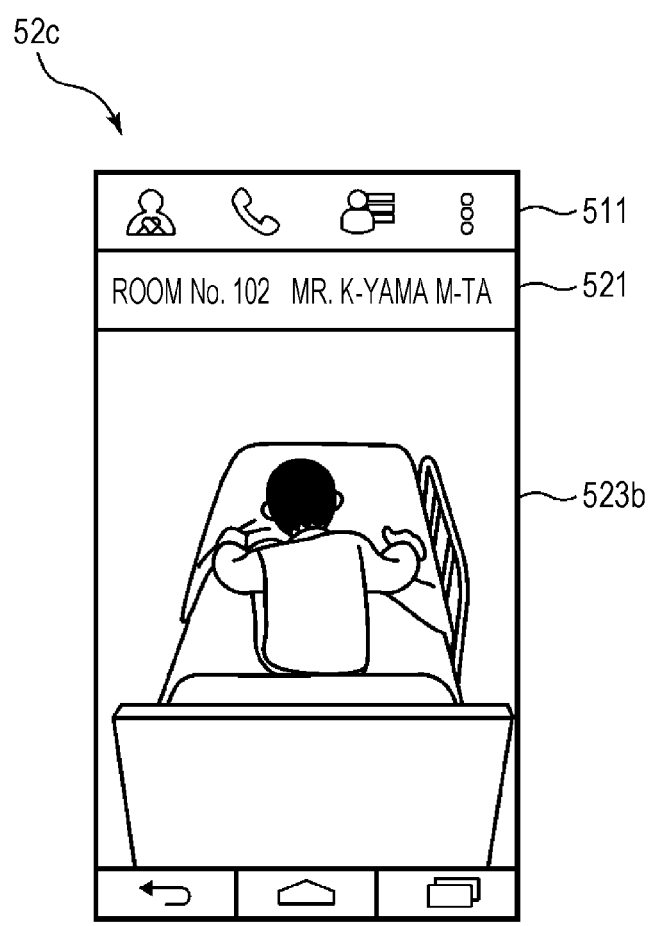
FIG. 8 illustrates one example of the monitoring information screen displayed in full screen in the mobile terminal unit.
Figure 9A:
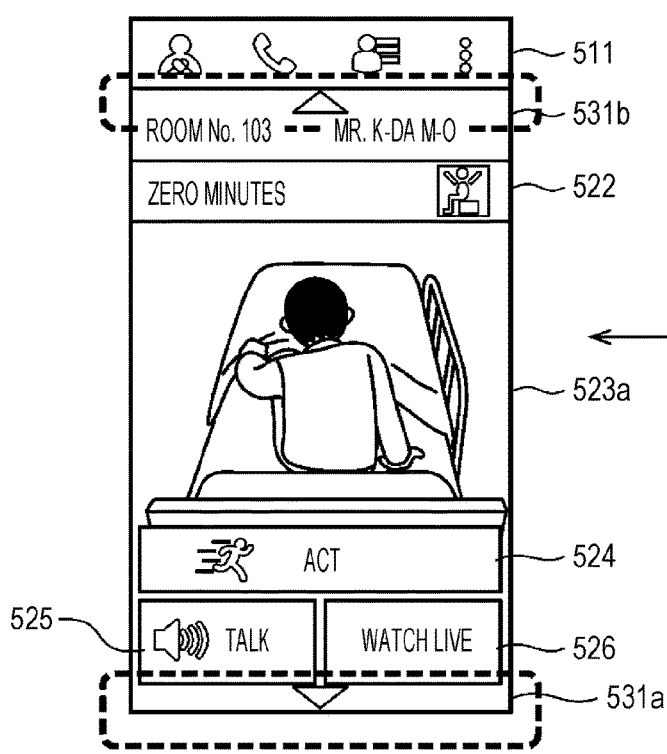
FIG. 9 illustrates one example of the monitoring information screen displayed in the mobile terminal unit having received the notification of a plurality of pieces of monitoring information on two or more different monitored persons.
Figure 9B:
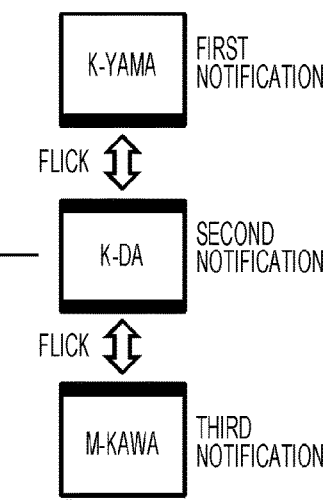

Next, description is made of the operation of displaying the monitoring information related to the monitoring of the monitored person Ob in the monitored-person monitoring system MS. FIG. 4 is a flowchart of the operation related to the display of the monitoring information in the mobile terminal unit. FIG. 5 illustrates one example of a standby screen displayed in the mobile terminal unit. FIG. 6 illustrates one example of the monitoring information screen displayed in the mobile terminal unit having received the notification that the monitored person has sat up in bed. FIG. 7 illustrates one example of the monitoring information screen displayed in the mobile terminal unit having received the notification of the monitoring information on a monitored person who is different from the monitored person who has already received the notification of the monitoring information. FIG. 8 illustrates one example of the monitoring information screen displayed in full screen in the mobile terminal unit. FIG. 9 illustrates one example of the monitoring information screen displayed in the mobile terminal unit having received the notification of a plurality of pieces of monitoring information on two or more different monitored persons. FIG. 9A illustrates the monitoring information screen and FIG. 9B illustrates the monitoring information screens that are arranged in the chronological order.

In FIG. 4, when the power is input to activate the mobile terminal unit TA and the mobile terminal unit TA accepts the log-in operation by a monitoring person (user) such as a nurse or a caregiver, the TA monitoring process unit 412 displays the standby screen in the TA display unit 46 to wait for the communication signal addressed to the own unit (S1). This standby screen 51 includes, as illustrated in FIG. 5 for example, a menu bar region 511 to display a menu bar, a standby main region 512 to display an icon and a message to express the standby state (for example, "no notification"), a time region 513 to display the current time, a date region 514 to display the today's year, month, day, and day of the week, and a user' name region 515 to display the user's name who currently logs in the mobile terminal unit TA.

Next, the TA control unit 411 of the mobile terminal unit TA determines whether the TA communication IF unit 43 has received the communication signal (S2). If the result of this determination indicates the communication signal has not been received (No), the mobile terminal unit TA returns the process to S1 and if the result of this determination indicates the communication signal has been received (Yes), the mobile terminal unit TA executes the next step S3.

In this step S3, if the communication signal is received, the TA monitoring process unit 412 of the mobile terminal unit TA determines whether the received communication signal is the monitoring information communication signal. If the result of determination indicates that the received communication signal is not the monitoring information communication signal (No), the TA control process unit 41 of the mobile terminal unit TA executes the process appropriate for the received communication signal (S21) and ends the display operation of the monitoring information. On the other hand, if the result of determination indicates that the received communication signal is the monitoring information communication signal (Yes), the TA monitoring process unit 412 of the mobile terminal unit TA registers the sensing ID, the determination result information, the determination time information, the image data of the still image, and the communication address to obtain the moving image that are contained in the received monitoring information communication signal in the monitoring information table MT, so that the TA monitoring information storage unit 422 stores these pieces of information while associating them with each other (S4) and the next step S5 is executed. Note that when each piece of information is registered in the monitoring information table MT, the TA monitoring process unit 412 registers the default flag "0" in each action field 4236.

In this step S5, the display process unit 4121 of the TA monitoring process unit 412 of the mobile terminal unit TA determines whether the other monitoring information screen 52 (52-A) for displaying the monitoring information on the monitored person Ob-A who is different from the monitored person Ob-B related to the monitoring information contained in the received monitoring information communication signal already exists, and the next step S6 is executed. More specifically, the display process unit 4121 of the TA monitoring process unit 412 determines whether the other monitoring information screen 52-A already exists by determining whether the sensing ID, which is different from the sensing ID contained in the received monitoring information communication signal, is registered in the sensing ID field 4231 in the record where the flag "0" is registered in the action field 4236. If the result of determination indicates that the sensing ID, which is different from the sensing ID contained in the received monitoring information communication signal, is not registered in the sensing ID field 4231 in the record where the flag "0" is registered in the action field 4236, it is determined that the monitoring information screen 52-A of the different sensing ID does not exist (No) and the mobile terminal unit TA executes the next step S6. On the other hand, if the result of determination indicates that the sensing ID, which is different from the sensing ID contained in the received monitoring information communication signal, is registered in the sensing ID field 4231 in the record where the flag "0" is registered in the action field 4236, it is determined that the monitoring information screen 52-A of the different sensing ID already exists (Yes) and the mobile terminal unit TA executes the next step S6. Note that the monitoring information screen 52 will be described in detail below.

In this step S6, the display process unit 4121 of the mobile terminal unit TA determines whether the monitoring information contained in the received monitoring information communication signal is the information on the sensing unit SU existing in the monitoring information screen 52. More specifically, the display process unit 4121 determines whether the monitoring information communication signal containing the same sensing ID as that contained in the received monitoring information communication signal is already received (in the past) before the received monitoring information communication signal and the monitoring information screen 52 of the already received monitoring information communication signal is created for the display. Further specifically, by determining whether the same sensing ID as that contained in the received monitoring information communication signal is registered in the sensing ID field 4231 in the record where the flag "0" is registered in the action field 4236, the display process unit 4121 determines whether the monitoring information screen 52 of the already received monitoring information communication signal is created for the display. If the result of determination indicates that the sensing ID, which is the same as the sensing ID contained in the received monitoring information communication signal, is not registered in the sensing ID field 4231 in the record where the flag "0" is registered in the action field 4236, it is determined that the monitoring information communication signal with the same sensing ID has not been received (No) and the mobile terminal unit TA executes step S7. On the other hand, if the result of determination indicates that the sensing ID, which is the same as the sensing ID contained in the received monitoring information communication signal, is registered in the sensing ID field 4231 in the record where the flag "0" is registered in the action field 4236, it is determined that the monitoring information communication signal with the same sensing ID has already been received (Yes) and the mobile terminal unit TA executes step S8.

In this step S7, the display process unit 4121 of the mobile terminal unit TA newly forms and stores the monitoring information screen 52 (52-B) in accordance with each piece of information (each piece of data) contained in the received monitoring information communication signal in the display screen storage unit 421.

This monitoring information screen 52 is the screen to display the monitoring information related to the monitoring of the monitored person Ob. The monitoring information screen 52 (52a) includes, for example as illustrated in FIG. 6: the menu bar region 511; a monitored-person's name region 521 which displays the place where the sensing unit SU with the sensing ID is installed and the name of the monitored person Ob to be monitored by the sensing unit SU with the sensing ID; an icon region 522 which displays the time passed after the determination time (or received time), and the icon expressing symbolically the determination result; an image region 523*a* which displays the image (here, the still image) taken by the sensing unit SU with the sensing ID; an "act" button 524; a "talk" button 525, and a "watch LIVE" button 526. The "act" button 524 is a button for the user of the mobile terminal unit TA to input to the mobile terminal unit TA that the user has the intention to take action, such as save life, nurse, take care of, or assist the monitored person Ob to be monitored by the sensing unit SU with the sensing ID, and input to the mobile terminal unit the instruction to notify the input of the intention to the fixed terminal unit SP and other mobile terminal unit TA. The "talk" button 525 is used to input the instruction to enable the conversation between the sensing unit SU with the sensing ID and the mobile terminal unit TA through the network NW. The "watch LIVE" button 526 is used to input the instruction to display the moving image taken by the sensing unit SU with the sensing ID.

In order to create the monitoring information screen 52-B in accordance with each piece of information contained in the received monitoring information communication signal, the display process unit 4121 searches for the installation place and the monitored-person's name for the sensing ID contained in the received monitoring information communication signal from the TA sensing unit information storage unit 423 using the sensing ID as the search key, calculates how long the time has passed since the determination time contained in the received monitoring information communication signal, and searches for the icon corresponding to the determination result contained in the received monitoring information communication signal from the TA storage unit 42 using the determination result as the search key. Note that each icon corresponding to each determination result is stored in advance in the TA storage unit 42 while being associated with the corresponding determination result. Then, the display process unit 4121 displays the menu bar in the menu bar region 511, displays the searched installation place and monitored-person's name in the monitored-person's name region 521, displays the calculated passed time and the searched icon in the icon region 522, displays the image (still image) contained in the received monitoring information communication signal in the image region 523*a*, and displays the "act" button 524, the "talk" button 525, and the "watch LIVE" button 526, so that a monitoring information screen 52*a* is formed and stored in the display screen storage unit 421.

In the case where the result of determination in step S5 indicates that the monitoring information screen 52-A with the different sensing ID already exists, forming such a new monitoring information screen 52-B in this manner causes the display process unit 4121 to store the newly formed monitoring information screen 52-B and the already existing monitoring information screen 52-A in the display screen storage unit 421 while associating these screens with each other in the chronological order. More specifically, the display process unit 4121 connects the newly formed monitoring information screen 52-B and the already existing monitoring information screen 52-A in the chronological order in the up-down direction when displayed in the TA display unit 46, and thus the screens are formed planarly.

Back to FIG. 4, in step S8, the display process unit 4121 of the mobile terminal unit TA updates the monitoring information screen 52 (52-B) in accordance with each piece of information (each piece of data) contained in the received monitoring information communication signal and forms and stores the updated screen in the display screen storage unit 421.

In order to update the monitoring information screen 52-B in accordance with each piece of information contained in the received monitoring information communication signal, the display process unit 4121 calculates the time passed since the determination time contained in the received monitoring information communication signal, and searches for the icon corresponding to the determination result contained in the received monitoring information communication signal from the TA storage unit 42 using the determination result as the search key. Then, the display process unit 4121 displays the obtained passed time and searched icon in the icon region 522 relative to the already existing monitoring information screen 52, and displays the image (still image) contained in the received monitoring information communication signal in the image region 523*a*, so that the monitoring information screen 52-B is updated and stored (formed) in the display screen storage unit 421. Here, the icon region 522 displays the icon in accordance with the determination result contained in the already received monitoring information communication signal; therefore, the currently searched icon is displayed in the icon region 522 with respect to the already displayed icon in the chronological order. For example, in the case where the determination result of the monitored person Ob "leave bed" is notified after "sit up in bed", the monitoring information screen 52*a* in FIG. 6 where the icon expressing the determination result of the monitored person Ob "sit up in bed" is displayed in the icon region 522 is updated in a manner that the icon expressing the determination result of the monitored person Ob "leave bed" is displayed in the icon region 522 on the left side of the icon expressing the determination result "sit up in bed" on the paper.

In the case where the result of determination in step S5 indicates that the monitoring information screen 52-A with the different sensing ID already exists, updating and forming the monitoring information screen 52-B in this manner causes the display process unit 4121 to store the updated and formed monitoring information screen 52-B and the already existing monitoring information screen 52-A in the display screen storage unit 421 while associating the screens with each other in the chronological order in a manner similar to step S7. More specifically, the display process unit 4121 connects the updated and formed monitoring information screen 52-B and the already existing monitoring information screen 52-A in the chronological order in the up-down direction when displayed in the TA display unit 46, and forms the screens planarly. Note that the display process unit 4121 may associate these screens with each other in the chronological order while maintaining the existing chronological relation (connection in the chronological order), or may reedit these screens while associating them in a new chronological order on the basis of the received monitoring information communication signal.

Next to step S7 or step S8, the TA control process unit 41 of the mobile terminal unit TA determines whether a predetermined input manipulation is accepted in the TA input unit 45 (S9). The predetermined input manipulation is to input to the mobile terminal unit TA the selection instruction as to whether the monitoring information screen 52 being displayed in the TA display unit 46 is continued or switched to the monitoring information screen 52 based on the monitoring information contained in the received monitoring information communication signal. The predetermined input manipulation is, for example in the present embodiment, also the input manipulation to input to the mobile terminal unit TA that the user of the mobile terminal unit TA (the person who monitors) is currently making a decision (considering, thinking) whether to take action, for example nurse the monitored person Ob, and corresponds to, for example, "tap". If the result of this determination indicates that the predetermined input manipulation (in this example, "tap") has not been accepted (No), the mobile terminal unit TA executes step S10; on the other hand, if the result of this determination indicates that the predetermined input manipulation (in this example, "tap") has been accepted (Yes), the mobile terminal unit TA executes step S11.

In this step S10, the display process unit 4121 of the mobile terminal unit TA displays the monitoring information screen 52-B based on the monitoring information contained in the received monitoring information communication signal, which is newly created in step S7 or updated in step S8, in the TA display unit 46. Thus, while the monitoring information screen 52-A expressing the monitoring information on the monitored person Ob-A is displayed, if the monitoring information on the other monitored person Ob-B has been received and the predetermined input manipulation (in this example, "tap") has not been accepted, the display process unit 4121 of the mobile terminal unit TA shifts the display from the monitoring information screen 52-A expressing the monitoring information on the monitored person Ob-A to the other monitoring information screen 52-B expressing the monitoring information on the different monitored person Ob-B. Then, the mobile terminal unit TA executes the next step S12.

In this step S11, the display process unit 4121 of the mobile terminal unit TA displays the different monitoring information reception display expressing the reception of the monitoring information communication signal containing the monitoring information on the other monitored person Ob-B, who is different from the monitored person Ob-A in the monitoring information screen 52-A that is currently displayed, in the monitoring information screen 52-A that is already displayed in the TA display unit 46. The different monitoring information reception display 531 is, for example, the stick-like display as illustrated in FIG. 7, and in the example illustrated in FIG. 7, additionally includes an inverted triangular mark (V) expressing that the monitoring information screen 52 (52-B) at the subsequent time follows the currently-displayed monitoring information screen 52b (52b-A) in the chronological order. Thus, while the monitoring information screen 52-A expressing the monitoring information on the monitored person Ob-A is displayed, if the monitoring information on the other monitored person Ob-B has been received and the predetermined input manipulation (in this example, "tap") has been accepted, the display process unit 4121 of the mobile terminal unit TA continues the display of the monitoring information screen 52-A expressing the monitoring information on the monitored person Ob-A. Then, the mobile terminal unit TA executes the next step S12.

Note that the display of the monitoring information screen 52-A may be continued only while the predetermined input manipulation is accepted, and upon the ending of the acceptance of the predetermined input manipulation, the display may be ended and the monitoring information screen 52-A may be shifted to the other monitoring information screen 52-B and the other monitoring information screen 52-B may be displayed. For example, the display of the monitoring information screen 52-A may be continued while the touch panel is touched and the ending of the touch may terminate the display of the monitoring information screen 52-A and the monitoring information screen 52-A may be shifted to the other monitoring information screen 52-B and the other monitoring information screen 52-B may be displayed. In addition, the display of the monitoring information screen 52-A may be continued for a predetermined period after the acceptance of the predetermined input manipulation. That is to say, during the predetermined period, it is regarded that the user is currently considering and in this case the predetermined input manipulation is being accepted (Yes in step S9). In an example in which the predetermined period is 20 seconds, the display of the monitoring information screen 52-A is continued for 20 seconds after the touch panel is "tapped", and after these 20 seconds, the display of the monitoring information screen 52-A may be ended and the other monitoring information screen 52-B may be displayed.

In step S11, upon accepting the "tap" as the input manipulation on the touch panel including the TA input unit 45 and the TA display unit 46, the TA control process unit 41 of the mobile terminal unit TA may display in the TA display unit 46 a monitoring information screen 52c in which the image region 523a is replaced by the image region 523b of the full-screen display. This monitoring information screen 52c includes, for example as illustrated in FIG. 8, the menu bar region 511, the monitored-person's name region 521, and the image region 523b of the full-screen display in which the image (here, the still image) taken by the sensing unit SU with the sensing ID is displayed entirely in the residual area excluding the menu bar region 511 and the monitored-person's name region 521. With this full-screen display, the person who monitors (user) can specifically recognize how the monitored person Ob is doing, and it becomes easier for the user to determine whether he takes action, for example nurses the monitored person Ob.

Back to FIG. 4, subsequent to step S10 or step S11, the TA control process unit 41 of the mobile terminal unit TA determines whether the touch panel including the TA input unit 45 and the TA display unit 46 has accepted the input manipulation (S12). If the result of this determination indicates that the input manipulation has not been accepted (No), the mobile terminal unit TA returns the process to step S12; on the other hand, if the result of this determination indicates that the input manipulation has been accepted, the mobile terminal unit TA executes the next step S13.

In this step S13, the TA control process unit 41 of the mobile terminal unit TA executes the process appropriate for the content of the input manipulation and ends the display operation of the monitoring information.

For example, upon accepting the input manipulation of the "act" button 524, the TA control process unit 41 of the mobile terminal unit TA registers the flag "1" in the action field 4236 in the record in which the sensing ID corresponding to the monitoring information on the monitored person Ob currently displayed in the TA display unit 46 is registered in the sensing ID field 4231, notifies the fixed terminal unit SP and another mobile terminal unit TA that the person who monitors (user) and currently logs in the mobile terminal unit TA has the intention to take action, for example nurse the monitored person Ob currently displayed in the TA display unit 46, and deletes the monitoring information screen 52 of the monitored person Ob displayed in the TA display unit 46.

In another example, upon accepting the input manipulation of the "talk" button 525, the TA control process unit 41 of the mobile terminal unit TA connects to the sensing unit SU which senses the monitored person Ob currently displayed in the TA display unit 46 through the network NW so that the conversation is possible.

In still another example, upon accepting the input manipulation of the "watch LIVE" button 526, the TA control process unit 41 of the mobile terminal unit TA connects to the sensing unit SU which monitors the monitored person Ob currently displayed in the TA display unit 46 through the network NW so that the moving image can be downloaded. This can display the moving image of the monitored person Ob in the image region 523*a*, or the image region 523*b* switched by the "tap".

In another example, upon accepting the "flick" input manipulation, the TA control process unit 41 of the mobile terminal unit TA shifts the display to the monitoring information screen 52 expressing the monitoring information corresponding to the different monitoring information reception display 531 displayed at the flick destination. For instance, in the example illustrated in FIG. 7, when the user "flicks" the display screen of the TA display unit 46 in the downward direction, the monitoring information screen 52-A that is currently displayed is shifted to the monitoring information screen 52-B expressing the monitoring information corresponding to the different monitoring information reception display 531 that is displayed at the flick destination, and the monitoring information screen 52-B is displayed. In another example, in the case where the plurality of monitoring information communication signals containing each piece of monitoring information on each of the different plural monitored persons Ob is received and there is the plurality of corresponding monitoring information screens 52, the following occurs: if there is the second monitoring information MI-t1 at the time before the first monitoring information MI-t2 corresponding to the first monitoring information display screen 52-t2, the display process unit 4121 causes the display screen storage unit 421 to store the first monitoring information screen 52-t2 and the second monitoring information screen 52-t1 expressing the second monitoring information MI-t1 while associating the screens with each other in the chronological order, and if there is the third monitoring information MI-t3 at the time after the first monitoring information MI-t2 corresponding to the first monitoring information display screen 52-t2, the display process unit 4121 causes the display screen storage unit 421 to store the first monitoring information screen 52-t2 and the third monitoring information screen 52-t3 expressing the third monitoring information MI-t3 while associating the screens with each other in the chronological order; and if there is the second monitoring information MI-t1 while the first monitoring information screen 52-t2 is displayed in the TA display unit 46, the display process unit 4121 displays the first different monitoring information reception display 531 expressing the reception of the second monitoring information MI-t1 on one end of the first monitoring information screen 52-t2, and if there is the third monitoring information MI-t3 while the first monitoring information screen 52-t2 is displayed in the TA display unit 46, the display process unit 4121 displays the second different monitoring information reception display 531 expressing the reception of the third monitoring information MI-t3 on the other end of the first monitoring information screen 52-t2. Upon the acceptance of the "flick" input manipulation, the display is shifted to the monitoring information screen 52 expressing the monitoring information corresponding to the different monitoring information reception display 531 displayed at the flick destination. For example, as illustrated in FIG. 9B, in the case where, among the second motoring information screen 52-t1 displaying the second monitoring information MI-t1 of "Mr. K-yama" as the second monitored person Ob-t1, the first monitoring information screen 52*d* (52-t2) displaying the first monitoring information MI-t2 of "Mr. K-da" as the first monitored person Ob-t2, and the third monitoring information screen 52-t3 displaying the third monitoring information MI-t3 of "Mr. M-kawa" as the third monitored person Ob-t3, the first monitoring information screen 52*d* (52-t2) is displayed on the display screen in the TA display unit 46 as illustrated in FIG. 9A, a first different monitoring information reception display 531*b* expressing the reception of the second monitoring information MI-t1 is displayed on one end of the first monitoring information screen 52*d* (52-t2), for example, at the upper end, and a third different monitoring information reception display 531*a* expressing the reception of the third monitoring information MI-t3 is displayed on the other end of the first monitoring information screen 52*d* (52-t2), for example, at the lower end. Then, when the display screen of the TA display unit 46 is "flicked" in the downward direction, the first monitoring information screen 52*d* (52-t2) that is currently displayed is shifted to the display of the third monitoring information screen 52-t3 expressing the third monitoring information MI-t3 corresponding to the different monitoring information reception display 531*a* displayed at the flick destination, and the third monitoring information screen 52-t3 is displayed. On the other hand, when the display screen of the TA display unit 46 is "flicked" in the upward direction, the first monitoring information screen 52*d* (52-t2) that is currently displayed is shifted to the display of the second monitoring information screen 52-t1 expressing the second monitoring information MI-t1 corresponding to the different monitoring information reception display 531*b* displayed at the flick destination, and the second monitoring information screen 52-t1 is displayed. Note that in FIG. 9, among the first to third monitoring information MI-t1 to MI-t3, the second monitoring information MI-t1 is received firstly, the first monitoring information MI-t2 is received secondly, and the third monitoring information MI-t3 is received thirdly.

As described above, according to the monitored-person monitoring system MS, the display device for the monitored-person monitoring system MS (typically, the mobile terminal unit TA in the above embodiment), and the display method for the monitored-person monitoring system which is implemented therein, in the case where the monitoring information screen 52 is currently displayed and a predetermined input manipulation such as the input manipulation to instruct the display device (mobile terminal unit TA) that the user is currently considering (in the above example, "tap") is accepted, the display of the monitoring information screen 52 that is currently displayed is continued even if the other monitoring information is received. Therefore, a plurality of pieces of monitoring information can be displayed as appropriate without displaying too many pieces of information, and it becomes easier to determine how to deal with the situation in accordance with the monitoring information. For example, the determination becomes difficult if the other monitoring information is received and the monitoring information screen 52 that is currently displayed is shifted to the other monitoring information screen 52 expressing the other monitoring information and the other monitoring information screen 52 is displayed, but this will not happen.

According to the monitored-person monitoring system MS, the display device for the monitored-person monitoring system MS (typically, the mobile terminal unit TA in the above embodiment), and the display method for the monitored-person monitoring system which is implemented therein, the different monitoring information reception display 531 is displayed; therefore, even if the display of the monitoring information screen 52 that is currently displayed is continued, the reception of the other monitoring information can be recognized.

According to the monitored-person monitoring system MS, the display device for the monitored-person monitoring system MS (typically, the mobile terminal unit TA in the above embodiment), and the display method for the monitored-person monitoring system which is implemented therein, the existence of the plurality of monitoring information screens 52 that is associated with each other in the chronological order can be recognized and moreover these screens can be sequentially displayed by the flick input manipulation in the present embodiment.

According to the monitored-person monitoring system MS, the display device for the monitored-person monitoring system MS (typically, the mobile terminal unit TA in the above embodiment), and the display method for the monitored-person monitoring system which is implemented therein, if the predetermined input manipulation ("tap" in the above-described example) has not been accepted, the monitoring information screen 52 that is currently displayed is shifted to the other monitoring information screen 52 expressing the other monitoring information. Therefore, the latest monitoring information can be displayed.

In the above embodiment, the monitored-person monitoring system MS is structured so that the sensing unit SU determines the state (status) of the monitored person Ob in order to reduce the amount of information processing of the management server unit SV. However, the monitored-person monitoring system MS may be alternatively structured so that the management server unit SV determines the state (status) of the monitored person Ob by receiving, for example, the output of the body motion sensor and the output of the image sensor from the sensing unit SU.

In the above embodiment, the mobile terminal unit TA corresponding to one example of the display device may be structured so as to be in the standby mode to wait for the input manipulation after a predetermined period after the end of accepting the predetermined input manipulation. More specifically, the mobile terminal unit TA corresponding to one example of the display device functionally has, additionally in the TA monitoring process unit 412, a mode control unit that sets the standby mode to wait for the input manipulation after a predetermined period after the end of accepting the predetermined input manipulation.

In the above embodiment, the mobile terminal unit TA corresponding to one example of the display device may be structured to, upon accepting the predetermined input manipulation, display the currently-considering screen expressing that the user is now considering whether to take action. More specifically, upon accepting the predetermined input manipulation in the TA input unit 45, the display process unit 4121 displays the currently-considering screen expressing that the user is now considering. Note that the monitoring information screen 52c having the full-screen display image region 523b illustrated in FIG. 8 may be one example of the currently-considering screen. The period for which this currently-considering screen is displayed may be regarded as the period for which the user is considering, and as the period for which the predetermined input manipulation is being accepted (Yes in step S9).

The shifting to the other monitoring information screen 52 associated in the chronological order occurs by "flick" in the above description but the manipulation is not limited to flick. For example, instead of "flick" or in addition to "flick", "tap" or "move the whole mobile terminal unit TA" may be employed. In the case of the "tap", the monitoring information display screen expressing the monitoring information corresponding to the different monitoring information reception display displayed at the "tapped" position is displayed. In the case of the "move the whole mobile terminal unit TA", the mobile terminal unit TA includes a triaxial acceleration sensor, and this triaxial acceleration sensor detects the moving direction when the mobile terminal unit TA is shaken or tilted, for example, and the monitoring information display screen expressing the monitoring information corresponding to the different monitoring information reception display displayed at the moving destination is displayed.

In the present specification, the techniques in various aspects as above are disclosed: the main techniques are summarized below.

A display device for a monitored-person monitoring system according to one aspect is a display device for a monitored-person monitoring system in which a predetermined behavior of each of a plurality of monitored persons as a monitoring target is sensed and notified, respectively, and the plurality of monitored persons is monitored, the display device receiving and displaying monitoring information on the monitored person, and while a monitoring information display screen expressing the monitoring information on a certain monitored person among the plurality of monitored persons is displayed, even if the monitoring information on another monitored person who is different from the certain monitored person among the plurality of monitored persons is received, the display of the monitoring information display screen expressing the monitoring information on the certain monitored person is continued as long as a predetermined input manipulation has been accepted. In another aspect, preferably, the display device for a monitored-person monitoring system is a display device for a monitored-person monitoring system in which each of a plurality of monitored persons as a monitoring target is sensed and the plurality of monitored persons is monitored, the display device receiving and displaying monitoring information on the monitored person, and including: a communication unit that performs communication; a display unit that performs display; an input unit that accepts an input manipulation; and a display process unit that, upon receiving a monitoring information communication signal containing the monitoring information in the communication unit, displays the monitoring information contained in the monitoring information communication signal in the display unit, wherein while a monitoring information display screen expressing the monitoring information on a certain monitored person among the plurality of monitored persons is displayed, even if the monitoring information communication signal containing the monitoring information on another monitored person who is different from the certain monitored person among the plurality of monitored persons is received, the display process unit continues the display of the monitoring information display screen expressing the monitoring information on the certain monitored person as long as a predetermined input manipulation has been accepted in the input unit.

In such a display device for a monitored-person monitoring system, if a predetermined input manipulation such as the input manipulation to instruct the display device that the user is currently considering has been accepted while the monitoring information display screen is displayed, the display of the monitoring information display screen that is currently displayed is continued even if the other monitoring information is received. Therefore, a plurality of pieces of monitoring information can be displayed as appropriate without displaying too many pieces of information, and it becomes easier to determine how to deal with the situation in accordance with the monitoring information. For example, the determination becomes difficult if the other monitoring information is received and the monitoring information screen that is currently displayed is shifted to the other monitoring information display screen expressing the other monitoring information and the other monitoring information display screen is displayed, but this will not happen.

In another aspect, the aforementioned display device for a monitored-person monitoring system displays a different monitoring information reception display expressing the reception of the monitoring information on the other monitored person on the monitoring information display screen expressing the monitoring information on the certain monitored person. In another aspect, preferably, in the aforementioned display device for a monitored-person monitoring system, the display process unit displays the different monitoring information reception display expressing the reception of the monitoring information on the other monitored person on the monitoring information display screen expressing the monitoring information on the certain monitored person.

Since such a display device for a monitored-person monitoring system displays the different monitoring information reception display, the reception of the other monitoring information can be recognized even if the display of the monitoring information display screen that is currently displayed is continued.

In another aspect, in the aforementioned display devices for a monitored-person monitoring system, if there is second monitoring information at the time before first monitoring information corresponding to a monitoring information display screen that is currently displayed, a first different monitoring information reception display expressing the reception of the second monitoring information is displayed on one end of the monitoring information display screen that is currently displayed, and if there is third monitoring information at the time after the first monitoring information corresponding to the monitoring information display screen that is currently displayed, the second different monitoring information reception display expressing the reception of the third monitoring information is displayed on the other end of the monitoring information display screen that is currently displayed. In another aspect, preferably, in the aforementioned display devices for a monitored-person monitoring system, if there is the second monitoring information at the time before the first monitoring information corresponding to the first monitoring information display screen, the display process unit causes the display screen storage unit to store the first monitoring information display screen and a second monitoring information display screen expressing the second monitoring information while associating the screens with each other in a chronological order, and if there is the third monitoring information at the time after the first monitoring information corresponding to the first monitoring information display screen, the display process unit causes the display screen storage unit to store the first monitoring information display screen and the third monitoring information display screen expressing the third monitoring information while associating the screens with each other in the chronological order; and if there is the second monitoring information while the first monitoring information display screen is displayed in the display unit, the display process unit displays the first different monitoring information reception display expressing the reception of the second monitoring information on one end of the first monitoring information display screen, and if there is the third monitoring information while the first monitoring information display screen is displayed in the display unit, the display process unit displays the second different monitoring information reception display expressing the reception of the third monitoring information on the other end of the first monitoring information display screen.

In such a display device for a monitored-person monitoring system, the existence of the plurality of monitoring information display screens that is associated with each other in chronological order can be recognized.

In another aspect, in the aforementioned display device for a monitored-person monitoring system, upon accepting a predetermined second input manipulation, which is different from the predetermined input manipulation, the display is shifted from the monitoring information display screen that is currently displayed to the display of the monitoring information display screen expressing the monitoring information corresponding to the different monitoring information reception display in accordance with the second input manipulation. In another aspect, preferably, in the aforementioned display device for a monitored-person monitoring system, upon accepting the predetermined second input manipulation, which is different from the predetermined input manipulation, in the input unit, the display process unit shifts the display from the first monitoring information display screen to the display of the monitoring information display screen expressing the monitoring information corresponding to the different monitoring information reception display in accordance with the second input manipulation. The second input manipulation is preferably at least one of flick, tap, and moving the whole display device. In the case of the flick, preferably, the monitoring information display screen expressing the monitoring information corresponding to the different monitoring information reception display displayed at the flick destination is displayed. In the case of the tap, preferably, the monitoring information display screen expressing the monitoring information corresponding to the different monitoring information reception display displayed at the tapped position is displayed. In the case of moving the whole display device, preferably, the monitoring information display screen expressing the monitoring information corresponding to the different monitoring information reception display displayed at the moving destination is displayed.

In such a display device for a monitored-person monitoring system, the plurality of monitoring information display screens that is associated with each other in the chronological order can sequentially be displayed by the second input manipulation.

In another aspect, the aforementioned display devices for a monitored-person monitoring system are set to the standby mode to wait for the input manipulation after a predetermined period after the end of accepting the predetermined input manipulation. In another aspect, preferably, the aforementioned display devices for a monitored-person monitoring system further include a mode control unit that sets a standby mode to wait for an input manipulation after a predetermined period after end of accepting the predetermined input manipulation.

With this structure, the display device for a monitored-person monitoring system which is set to the standby mode to wait for the input manipulation after a predetermined period after the end of accepting the predetermined input manipulation can be provided.

In another aspect, the aforementioned display devices for a monitored-person monitoring system display, upon accepting the predetermined input manipulation, a currently-considering screen expressing that a user of the display device is considering whether to take action for the monitored person. In another aspect, preferably, in the aforementioned display devices for a monitored-person monitoring system, upon accepting the predetermined input manipulation in the input unit, the display process unit displays the currently-considering screen expressing that the user of the display device is currently considering whether to take action for the monitored person.

According to this structure, the display device for a monitored-person monitoring system, which displays the currently-considering screen upon accepting the predetermined input manipulation in the input unit, can be provided.

In another aspect, the aforementioned display devices for a monitored-person monitoring system have the monitoring information display screen expressing the monitoring information on the certain monitored person and the other monitoring information display screen expressing the monitoring information on the other monitored person that are arranged in the chronological order, and while the monitoring information display screen expressing the monitoring information on the certain monitored person is displayed, if the monitoring information on the other monitored person is received and the predetermined input manipulation has not been accepted, the display is shifted from the monitoring information display screen expressing the monitoring information on the certain monitored person to the other monitoring information display screen expressing the monitoring information on the other monitored person. In another aspect, preferably, the aforementioned display devices for a monitored-person monitoring system further include a display screen storage unit that stores a display screen, and the display process unit causes the display screen storage unit to store the monitoring information display screen expressing the monitoring information on the certain monitored person and the other monitoring information display screen expressing the monitoring information on the other monitored person while associating the screens with each other in the chronological order, and while the monitoring information display screen expressing the monitoring information on the certain monitored person is displayed, if the monitoring information communication signal containing the monitoring information on the other monitored person is received and the predetermined input manipulation has not been accepted, the display process unit shifts the display in the display unit from the monitoring information display screen expressing the monitoring information on the certain monitored person to the other monitoring information display screen expressing the monitoring information on the other monitored person.

In such a display device for a monitored-person monitoring system, if the predetermined input manipulation has not been accepted, the display is shifted from the monitoring information display screen that is currently displayed to the other monitoring information display screen expressing the other monitoring information; therefore, the latest monitoring information can be displayed.

A display method for a monitored-person monitoring system according to another aspect is a display method for a monitored-person monitoring system in which a predetermined behavior of each of a plurality of monitored persons as a monitoring target is sensed and notified and the plurality of monitored persons is monitored. In the display method, the monitoring information on the monitored person is received and displayed. While the monitoring information display screen expressing the monitoring information on the certain monitored person among the plurality of monitored persons is displayed, even if the monitoring information on the other monitored person who is different from the certain monitored person among the plurality of monitored persons is received, the display of the monitoring information display screen expressing the monitoring information on the certain monitored person is continued as long as a predetermined input manipulation has been accepted. In another aspect, preferably, the display method for a monitored-person monitoring system is a display method for a monitored-person monitoring system in which each of a plurality of monitored persons as a monitoring target is sensed and the plurality of monitored persons is monitored, the display method receiving monitoring information on the monitored person and displaying the information on a display device, and the display method includes: an input step of accepting an input manipulation; and a display process step of, upon reception of a monitoring information communication signal containing the monitoring information in a communication unit that performs communication, displaying the monitoring information contained in the monitoring information communication signal in a display unit that performs display, wherein while a monitoring information display screen expressing the monitoring information on a certain monitored person among the plurality of monitored persons is displayed, even if the monitoring information communication signal containing the monitoring information on another monitored person who is different from the certain monitored person among the plurality of monitored persons is received, the display of the monitoring information display screen expressing the monitoring information on the certain monitored person is continued in the display process step as long as a predetermined input manipulation has been accepted in the input step.

A monitored-person monitoring system according to another aspect is a monitored-person monitoring system including: a display device; and a sensing device that is connected to the display device so that communication with the display device is possible, senses each of a plurality of monitored persons as a monitoring target, and notifies a sensing result to the display device, and the display device is any one of the aforementioned display devices.

According to the display method for the monitored-person monitoring system and the monitored-person monitoring system, while the monitoring information display screen is displayed, even if the other monitoring information is received, the display of the monitoring information display screen that is currently displayed is continued as long as the predetermined input manipulation, for example, the input manipulation to instruct that the user is currently considering to the display device has been accepted. Therefore, the display of too many pieces of information can be avoided and the plurality of pieces of monitoring information can be displayed as appropriate and it becomes easier to determine how to deal with the situation in accordance with the monitoring information.

This application claims priority from Japanese Patent Application No. 2015-65286 filed with the Japan Patent Office on Mar. 26, 2015, the entire content of which is hereby incorporated by reference.

In order to express the present invention, the present invention has been sufficiently described as appropriate through the embodiment with reference to the drawings, but it is to be understood that the above embodiment can easily be changed and/or modified by a person skilled in the art.

Therefore, unless such change and modification made by the person skilled in the art depart from the scope of rights according to the scope of claims, the change and the modification are construed as being incorporated in the scope of rights according to the claims.

INDUSTRIAL APPLICABILITY

According to the present invention, the display device and the display method for the monitored-person monitoring system, and the monitored-person monitoring system can be provided.

The invention claimed is:

1. A display device for a monitored-person monitoring system in which each of a plurality of monitored persons as a monitoring target is sensed and the plurality of monitored persons is monitored, the display device receiving and displaying monitoring information on the monitored person, and comprising:

a communicator that performs communication;
a display that performs display;
an input that accepts an input manipulation; and
a display processor that, upon receiving a monitoring information communication signal containing the monitoring information in the communicator, displays the monitoring information contained in the monitoring information communication signal in the display, wherein while a monitoring information display screen expressing the monitoring information on a certain monitored person among the plurality of monitored persons is displayed, even if the monitoring information communication signal containing the monitoring information on another monitored person who is different from the certain monitored person among the plurality of monitored persons is received, the display processor continues the display of the monitoring information display screen expressing the monitoring information on the certain monitored person as long as a predetermined input manipulation has been accepted in the input;

if the predetermined input manipulation has not been accepted, the display processor shifts the display in the display from the monitoring information display screen expressing the monitoring information on the certain monitored person to the other monitoring information display screen expressing the monitoring information on the other monitored person; and the monitoring information display screen can accept an input manipulation of a user intention to take action against a certain monitored person.

2. The display device for a monitored-person monitoring system according to claim 1, wherein the display processor displays a different monitoring information reception display expressing reception of the monitoring information on the other monitored person on the monitoring information display screen expressing the monitoring information on the certain monitored person.

3. The display device for a monitored-person monitoring system according to claim 1, wherein if there is second monitoring information at a time before first monitoring information corresponding to a first monitoring information display screen, the display processor causes the display screen display storage to store the first monitoring information display screen and a second monitoring information display screen expressing the second monitoring information while associating the screens with each other in a chronological order, and if there is third monitoring information at a time after the first monitoring information corresponding to the first monitoring information display screen, the display processor causes the display screen storage to store the first monitoring information display screen and a third monitoring information display screen expressing the third monitoring information while associating the screens with each other in the chronological order, and if there is the second monitoring information while the first monitoring information display screen is displayed in the display, the display processor displays a first different monitoring information reception display expressing reception of the second monitoring information on one end of the first monitoring information display screen, and if there is the third monitoring information while the first monitoring information display screen is displayed in the display, the display processor displays a second different monitoring information reception display expressing reception of the third monitoring information on the other end of the first monitoring information display screen.

4. The display device for a monitored-person monitoring system according to claim 3, wherein upon accepting a predetermined second input manipulation, which is different from the predetermined input manipulation, in the input, the display processor shifts the display from the first monitoring information display screen to the monitoring information display screen expressing the monitoring information corresponding to the different monitoring information reception display in accordance with the second input manipulation.

5. The display device for a monitored-person monitoring system according to claim 4, wherein the second input manipulation is at least one of flick, tap, and moving the whole display device.

6. The display device for a monitored-person monitoring system according to claim 1, further comprising a mode controller that sets a standby mode to wait for an input manipulation after a predetermined period after end of accepting the predetermined input manipulation.

7. The display device for a monitored-person monitoring system according to claim 1, wherein upon accepting the predetermined input manipulation in the input, the display processor displays a currently-considering screen expressing that a user of the display device is considering whether to take action for the monitored person.

8. The display device for a monitored-person monitoring system according to claim 1, further comprising a display screen storage that stores a display screen, wherein the display processor causes the display screen storage to store the monitoring information display screen expressing the monitoring information on the certain monitored person and the other monitoring information display screen expressing the monitoring information on the other monitored person while associating the screens with each other in the chronological order.

9. A display method for a monitored-person monitoring system in which each of a plurality of monitored persons as a monitoring target is sensed and the plurality of monitored persons is monitored, the display method receiving monitoring information on the monitored person and displaying the information on a display device, and comprising:

accepting an input manipulation; and upon reception of a monitoring information communication signal containing the monitoring information in a communicator that performs communication, displaying the monitoring information contained in the monitoring information communication signal in a display that performs display, wherein while a monitoring information display screen expressing the monitoring information on a certain monitored person among the plurality of monitored persons is displayed, even if the monitoring information communication signal containing the monitoring information on another monitored person who is different from the certain monitored person among the plurality of monitored persons is received, the display of the monitoring information display screen expressing the monitoring information on the certain monitored person is continued in the displaying as long as a predetermined input manipulation has been accepted in the accepting;

if the predetermined input manipulation has not been accepted, the display processor shifts the display in the display from the monitoring information display screen expressing the monitoring information on the certain monitored person to the other monitoring information display screen expressing the monitoring information on the other monitored person; and the monitoring information display screen can accept an input manipulation of a user intention to take action against a certain monitored person.

10. A monitored-person monitoring system comprising:
a display device; and
a sensing device that is connected to the display device so that communication with the display device is possible, senses each of a plurality of monitored persons as a monitoring target, and notifies a sensing result to the display device, wherein
the display device is the display device according to claim 1.

11. The display device for a monitored-person monitoring system according to claim 2, wherein
if there is second monitoring information at a time before first monitoring information corresponding to a first monitoring information display screen, the display processor causes the display screen display storage to store the first monitoring information display screen and a second monitoring information display screen expressing the second monitoring information while associating the screens with each other in a chronological order, and if there is third monitoring information at a time after the first monitoring information corresponding to the first monitoring information display screen, the display processor causes the display screen storage to store the first monitoring information display screen and a third monitoring information display screen expressing the third monitoring information while associating the screens with each other in the chronological order, and
if there is the second monitoring information while the first monitoring information display screen is displayed in the display, the display processor displays a first different monitoring information reception display expressing reception of the second monitoring information on one end of the first monitoring information display screen, and if there is the third monitoring information while the first monitoring information display screen is displayed in the display, the display processor displays a second different monitoring information reception display expressing reception of the third monitoring information on the other end of the first monitoring information display screen.

12. The display device for a monitored-person monitoring system according to claim 2, further comprising a mode controller that sets a standby mode to wait for an input manipulation after a predetermined period after end of accepting the predetermined input manipulation.

13. The display device for a monitored-person monitoring system according to claim 2, wherein
upon accepting the predetermined input manipulation in the input, the display processor displays a currently-considering screen expressing that a user of the display device is considering whether to take action for the monitored person.

14. The display device for a monitored-person monitoring system according to claim 2, further comprising a display screen storage that stores a display screen, wherein
the display processor causes the display screen storage to store the monitoring information display screen expressing the monitoring information on the certain monitored person and the other monitoring information display screen expressing the monitoring information on the other monitored person while associating the screens with each other in the chronological order, and while the monitoring information display screen expressing the monitoring information on the certain monitored person is displayed, if the monitoring information communication signal containing the monitoring information on the other monitored person is received and the predetermined input manipulation has not been accepted, the display processor shifts the display in the display from the monitoring information display screen expressing the monitoring information on the certain monitored person to the other monitoring information display screen expressing the monitoring information on the other monitored person.

15. A monitored-person monitoring system comprising:
a display device; and
a sensing device that is connected to the display device so that communication with the display device is possible, senses each of a plurality of monitored persons as a monitoring target, and notifies a sensing result to the display device, wherein
the display device is the display device according to claim 2.

16. The display device for a monitored-person monitoring system according to claim 3, further comprising a mode controller that sets a standby mode to wait for an input manipulation after a predetermined period after end of accepting the predetermined input manipulation.

17. The display device for a monitored-person monitoring system according to claim 3, wherein
upon accepting the predetermined input manipulation in the input, the display processor displays a currently-considering screen expressing that a user of the display device is considering whether to take action for the monitored person.

18. The display device for a monitored-person monitoring system according to claim 3, further comprising a display screen storage that stores a display screen, wherein
the display processor causes the display screen storage to store the monitoring information display screen expressing the monitoring information on the certain monitored person and the other monitoring information display screen expressing the monitoring information on the other monitored person while associating the screens with each other in the chronological order.

19. A monitored-person monitoring system comprising:
a display device; and
a sensing device that is connected to the display device so that communication with the display device is possible, senses each of a plurality of monitored persons as a monitoring target, and notifies a sensing result to the display device, wherein
the display device is the display device according to claim 3.

20. The display device for a monitored-person monitoring system according to claim 4, further comprising a mode controller that sets a standby mode to wait for an input manipulation after a predetermined period after end of accepting the predetermined input manipulation.

* * * * *